US012758649B2

(12) United States Patent
Kamat et al.

(10) Patent No.: US 12,758,649 B2
(45) Date of Patent: Oct. 13, 2026

(54) PHASE-SEGREGATED VESICLES FOR SPATIALLY CONTROLLED PROTEIN-CONJUGATION AND CELL THERAPY

(71) Applicant: Northwestern University, Evanston, IL (US)

(72) Inventors: Neha Prashant Kamat, Evanston, IL (US); Justin Alexander Peruzzi, Evanston, IL (US); Timothy Quang Vu, Evanston, IL (US)

(73) Assignee: Northwestern University, Evanston, IL (US)

( * ) Notice: Subject to any disclaimer, the term of this patent is extended or adjusted under 35 U.S.C. 154(b) by 386 days.

(21) Appl. No.: 17/827,325

(22) Filed: May 27, 2022

(65) Prior Publication Data

US 2022/0378940 A1 Dec. 1, 2022

Related U.S. Application Data

(60) Provisional application No. 63/202,121, filed on May 27, 2021.

(51) Int. Cl.

| | |
|---|---|
| ***A61K 48/00*** | (2006.01) |
| ***A61K 9/00*** | (2006.01) |
| ***A61K 9/1272*** | (2025.01) |
| ***A61K 47/68*** | (2017.01) |
| ***A61K 47/69*** | (2017.01) |

(52) U.S. Cl.

CPC ........ *A61K 48/0025* (2013.01); *A61K 9/0019* (2013.01); *A61K 9/1272* (2013.01); *A61K 47/6811* (2017.08); *A61K 47/6911* (2017.08)

(58) Field of Classification Search

None

See application file for complete search history.

(56) References Cited

U.S. PATENT DOCUMENTS 6,761,902 B2 * 7/2004 Sodroski .............. A61K 9/1271 264/4.1

2012/0277158 A1 * 11/2012 Castaigne ............... A61P 35/04 977/788

OTHER PUBLICATIONS

Miguel et al., Liposomes Decorated with Apo2L/TRAIL Overcome Chemoresistance of Human Hematologic Tumor Cells, Mol. Pharmaceutics 2013, 10, 893-904, published Jan. 18, 2013 (Year: 2013).*

Millipore Sigma, 18:1 DGS-NTA(NI), https://www.sigmaaldrich.com/US/en/product/avanti/790404p?srsltid=AfmBOopuW3F6_7yrzeABZwx502FGUf7FtlwbXoyccnvkOJc_cpbCqWGm (Year: 2025).*

Pubcompare, Rho dope, https://www.pubcompare.ai/product/Pp3FHJMBdNj 1hjtAOpFI/ (Year: 2025).*

Wajant, H.; Moosmayer, D.; Wüest, T.; Bartke, T.; Gerlach, E.; Schönherr, U.; Peters, N.; Scheurich, P.; Pfizenmaier, K. Differential Activation of TRAIL-R1 and -2 by Soluble and Membrane TRAIL Allows Selective Surface Antigen-Directed Activation of TRAIL-R2 by a Soluble TRAIL Derivative. Oncogene 2001, 20, 4101-4106.

Wang, Y.; Baars, I.; Fördös, F.; Högberg, B. Clustering of Death Receptor for Apoptosis Using Nanoscale Patterns of Peptides. ACS Nano 2021, 15, 9614-9626.

Ye, K.; Wang, X.; Cao, L.; Li, S.; Li, Z.; Yu, L.; Ding, J. Matrix Stiffness and Nanoscale Spatial Organization of Cell-Adhesive Ligands Direct Stem Cell Fate. Nano Lett. 2015, 15, 4720-4729.

Zakaria, A. B.; Picaud, F.; Rattier, T.; Pudlo, M.; Saviot, L.; Chassagnon, R.; Lherminier, J.; Gharbi, T.; Micheau, O.; Herlem, G. Nanovectorization of TRAIL with Single Wall Carbon Nanotubes Enhances Tumor Cell Killing. Nano Lett. 2015, 15, 891-895.

Zhang, Q.; Reinhard, B. M. Ligand Density and Nanoparticle Clustering Cooperate in the Multivalent Amplification of Epidermal Growth Factor Receptor Activation. ACS Nano 2018, 12, 10473-10485.

Zhao, J.; Wu, J.; Heberle, F. A.; Mills, T. T.; Klawitter, P.; Huang, G.; Costanza, G.; Feigenson, G. W. Phase Studies of Model Biomembranes: Complex Behavior of DSPC/DOPC/Cholesterol. Biochim. Biophys. Acta—Biomembr. 2007, 1768, 2764-2776.

Liu et al. Dipolar Janus Liposomes: Formation, Electrokinetic Motion and Self-Assembly. Soft Matter. 2020. 27 pages.

Wang et al. Janus Liposomes: Gel-Assisted Formation and Bioaffinity-Directed Clustering. Langmuir 2018, 34, 25, 7509-7518.

Rahman et al. Spontaneous Formation of Gating Lipid Domain in Uniform-Size Peptide Vesicles for Controlled Release. J Am Chem Soc. Dec. 26, 2018; 140(51): 17956-17961.

Almeda, D.; Wang, B.; Auguste, D. T. Minimizing Antibody Surface Density on Liposomes While Sustaining Cytokine-Activated EC Targeting. Biomaterials 2015, 41, 37-44.

Berg, D.; Stühmer, T.; Siegmund, D.; Müller, N.; Giner, T.; Dittrich-Breiholz, O.; Kracht, M.; Bargou, R.; Wajant, H. Oligomerized Tumor Necrosis Factor-Related Apoptosis Inducing Ligand Strongly Induces Cell Death in Myeloma Cells, but Also Activates Proinflammatory Signaling Pathways. FEBS J. 2009, 276, 6912-6927.

Berger, R. M. L.; Weck, J. M.; Kempe, S. M.; Hill, O.; Liedl, T.; Rädler, J. O.; Monzel, C.; Heuer-Jungemann, A. Nanoscale FasL Organization on DNA Origami to Decipher Apoptosis Signal Activation in Cells. Small 2021, 17, 2101678.

Beyrath, J.; Chekkat, N.; Smulski, C. R.; Lombardo, C. M.; Lechner, M.-C.; Seguin, C.; Decossas, M.; Spanedda, M. V.; Frisch, B.; Guichard, G.; Fournel, S.; Beyrath, J.; Chekkat, N.; Smulski, C. R.; Lombardo, C. M.; Lechner, M.-C.; Seguin, C.; Decossas, M.; Spanedda, M. V.; Frisch, B.; Guichard, G.; Fournel, S. Synthetic Ligands of Death Receptor 5 Display a Cell-Selective Agonistic Effect at Different Oligomerization Levels. Oncotarget 2016, 7, 64942-64956.

(Continued)

*Primary Examiner* — Anna R Falkowitz
*Assistant Examiner* — Edwin Coleman Mitchell
(74) *Attorney, Agent, or Firm* — Quarles & Brady LLP

(57) ABSTRACT

The present invention provides compositions comprising phase separated nanoparticles, as well as methods of making the nanoparticles and uses thereof. The nanoparticles can be conjugated to therapeutics and used to treat diseases or to screen compounds.

10 Claims, 14 Drawing Sheets

(56) References Cited

OTHER PUBLICATIONS

Bin, L.; Thorburn, J.; Thomas, L. R.; Clark, P. E.; Humphreys, R.; Thorburn, A. Tumor-Derived Mutations in the TRAIL Receptor DR5 Inhibit TRAIL Signaling through the DR4 Receptor by Competing for Ligand Binding. J. Biol. Chem. 2007, 282, 28189-28194.
Brodszkij, E.; Westensee, I. N.; Bertelsen, M.; Gal, N.; Boesen, T.; Städler, B. Polymer-Lipid Hybrid Vesicles and Their Interaction with HepG2 Cells. Small 2020, 16, 1906493.
Chen, B.; Jia, Y.; Gao, Y.; Sanchez, L.; Anthony, S. M.; Yu, Y. Janus Particles as Artificial Antigen-Presenting Cells for T Cell Activation. ACS Appl. Mater. Interfaces 2014, 6, 18435-18439.
Chen, Z.; Wholey, W.-Y.; Hassani Najafabadi, A.; Moon, J. J.; Grigorova, I.; Chackerian, B.; Cheng, W. Self-Antigens Displayed on Liposomal Nanoparticles above a Threshold of Epitope Density Elicit Class-Switched Autoreactive Antibodies Independent of T Cell Help. J. Immunol. 2020, 204, 335-347.
Christian, D. A.; Tian, A.; Ellenbroek, W. G.; Levental, I.; Rajagopal, K.; Janmey, P. A.; Liu, A. J.; Baumgart, T.; Discher, D. E. Spotted Vesicles, Striped Micelles and Janus Assemblies Induced by Ligand Binding. Nat. Mater. 2009 810 2009, 8, 843-849.
Cornell, C. E.; Mileant, A.; Thakkar, N.; Lee, K. K.; Keller, S. L. Direct Imaging of Liquid Domains in Membranes by Cryo-Electron Tomography. Proc. Natl. Acad. Sci. U. S. A. 2020, 117, 19713-19719.
Dao, T. P. T.; Fernandes, F.; Er-Rafik, M.; Salva, R.; Schmutz, M.; Brûlet, A.; Prieto, M.; Sandre, O.; Le Meins, J. F. Phase Separation and Nanodomain Formation in Hybrid Polymer/Lipid Vesicles. ACS Macro Lett. 2015, 4, 182-186.
De Miguel, D.; Gallego-Lleyda, A.; Anel, A.; Martinez-Lostao, L. Liposome-Bound TRAIL Induces Superior DR5 Clustering and Enhanced DISC Recruitment in Histiocytic Lymphoma U937 Cells. Leuk. Res. 2015, 39, 657-666.
De Miguel, D.; Gallego-Lleyda, A.; Ayuso, J. M.; Pejenaute-Ochoa, D.; Jarauta, V.; Marzo, I.; Fernández, L. J.; Ochoa, I.; Conde, B.; Anel, A.; Martinez-Lostao, L. High-Order TRAIL Oligomer Formation in TRAIL-Coated Lipid Nanoparticles Enhances DR5 Cross-Linking and Increases Antitumour Effect against Colon Cancer. Cancer Lett. 2016, 383, 250-260.
Elson, E. L.; Fried, E.; Dolbow, J. E.; Genin, G. M. Phase Separation in Biological Membranes: Integration of Theory and Experiment. http://dx.doi.org/10.1146/annurev.biophys.093008.131238 2010, 39, 207-226.
Gonda, A.; Kabagwira, J.; Senthil, G. N.; Wall, N. R. Internalization of Exosomes through Receptor-Mediated Endocytosis. Mol. Cancer Res. 2019, 17, 337-347.
Gunawan, R. C.; Auguste, D. T. The Role of Antibody Synergy and Membrane Fluidity in the Vascular Targeting of Immunoliposomes. Biomaterials 2010, 31, 900-907.
Heberle, F. A.; Doktorova, M.; Scott, H. L.; Skinkle, A. D.; Waxham, M. N.; Levental, I. Direct Label-Free Imaging of Nanodomains in Biomimetic and Biological Membranes by Cryogenic Electron Microscopy. Proc. Natl. Acad. Sci. U.S.A. 2020, 117, 19943-19952.
Imam, Z. I.; Kenyon, L. E.; Ashby, G.; Nagib, F.; Mendicino, M.; Zhao, C.; Gadok, A. K.; Stachowiak, J. C. Phase-Separated Liposomes Enhance the Efficiency of Macromolecular Delivery to the Cellular Cytoplasm. Cell. Mol. Bioeng. 2017, 10, 387-403.
Jyotsana, N.; Zhang, Z.; Himmel, L. E.; Yu, F.; King, M. R. Minimal Dosing of Leukocyte Targeting TRAIL Decreases Triple-Negative Breast Cancer Metastasis Following Tumor Resection. Sci. Adv. 2019, 5, eaaw4197.
Kelley, R. F.; Totpal, K.; Lindstrom, S. H.; Mathieu, M.; Billeci, K.; DeForge, L.; Pai, R.; Hymowitz, S. G.; Ashkenazi, A. Receptor-Selective Mutants of Apoptosis-Inducing Ligand 2/Tumor Necrosis Factor-Related Apoptosis-Inducing Ligand Reveal a Greater Contribution of Death Receptor (DR) 5 than DR4 to Apoptosis Signaling. J. Biol. Chem. 2005, 280, 2205-2212.
Kern, N.; Dong, R.; Douglas, S. M.; Vale, R. D.; Morrissey, M. A. Tight Nanoscale Clustering of FcγReceptors Using DNA Origami Promotes Phagocytosis. Elife 2021, 10, 1-29.
Kischkel, F. C.; Lawrence, D. A.; Chuntharapai, A.; Schow, P.; Kim, K. J.; Ashkenazi, A. Apo2L/TRAIL-Dependent Recruitment of Endogenous FADD and Caspase-8 to Death Receptors 4 and 5. Immunity 2000, 12, 611-620.
Le, D. H. T.; Commandeur, U.; Steinmetz, N. F. Presentation and Delivery of Tumor Necrosis Factor-Related Apoptosis-Inducing Ligand via Elongated Plant Viral Nanoparticle Enhances Antitumor Efficacy. ACS Nano 2019, 13, acsnano.8b09462.
Lee, K.; Yu, Y. Janus Nanoparticles for T Cell Activation: Clustering Ligands to Enhance Stimulation. J. Mater. Chem. B 2017, 5, 4410-4415.
Lemke, J.; Noack, A.; Adam, D.; Tchikov, V.; Bertsch, U.; Röder, C.; Schütze, S.; Wajant, H.; Kalthoff, H.; Trauzold, A. TRAIL Signaling Is Mediated by DR4 in Pancreatic Tumor Cells despite the Expression of Functional DR5. J. Mol. Med. 2010, 88, 729-740.
Liu, J.; Toy, R.; Vantucci, C.; Pradhan, P.; Zhang, Z.; Kuo, K. M.; Kubelick, K. P.; Huo, D.; Wen, J.; Kim, J.; Lyu, Z.; Dhal, S.; Atalis, A.; Ghosh-Choudhary, S. K.; Devereaux, E. J.; Gumbart, J. C.; Xia, Y.; Emelianov, S. Y.; Willett, N. J.; Roy, K. Bifunctional Janus Particles as Multivalent Synthetic Nanoparticle Antibodies (SNAbs) for Selective Depletion of Target Cells. Nano Lett. 2021, acs.nanolett.0c04833.
Marconi, M.; Ascione, B.; Ciarlo, L.; Vona, R.; Garofalo, T.; Sorice, M.; Gianni, A. M.; Locatelli, S. L.; Carlo-Stella, C.; Malorni, W.; Matarrese, P. Constitutive Localization of DR4 in Lipid Rafts Is Mandatory for TRAIL-Induced Apoptosis in B-Cell Hematologic Malignancies. Cell Death Dis. 2013, 4, e863-e863.
Mitchell, M. J.; Wayne, E.; Rana, K.; Schaffer, C. B.; King, M. R. TRAIL-Coated Leukocytes That Kill Cancer Cells in the Circulation. Proc. Natl. Acad. Sci. 2014, 111, 930-935.
Mitchell, M. J.; Webster, J.; Chung, A.; Guimarães, P. P. G.; Khan, O. F.; Langer, R. Polymeric Mechanical Amplifiers of Immune Cytokine-Mediated Apoptosis. Nat. Commun. 2017, 8, 14179.
Moody, P. R.; Sayers, E. J.; Magnusson, J. P.; Alexander, C.; Borri, P.; Watson, P.; Jones, A. T. Receptor Crosslinking: A General Method to Trigger Internalization and Lysosomal Targeting of Therapeutic Receptor: Ligand Complexes. Mol. Ther. 2015, 23, 1888-1898.
Nair, P. M.; Flores, H.; Gogineni, A.; Marsters, S.; Lawrence, D. A.; Kelley, R. F.; Ngu, H.; Sagolla, M.; Komuves, L.; Bourgon, R.; Settleman, J.; Ashkenazi, A. Enhancing the Antitumor Efficacy of a Cell-Surface Death Ligand by Covalent Membrane Display. Proc. Natl. Acad. Sci. 2015, 112, 5679-5684.
Natoni, A.; MacFarlane, M.; Inoue, S.; Walewska, R.; Majid, A.; Knee, D.; Stover, D. R.; Dyer, M. J. S.; Cohen, G. M. Trail Signals to Apoptosis in Chronic Lymphocytic Leukaemia Cells Primarily through TRAIL-R1 Whereas Cross-Linked Agonistic TRAIL-R2 Antibodies Facilitate Signalling via TRAIL-R2. Br. J. Haematol. 2007, 139, 568-577.
Ortiz-Otero, N.; Marshall, J. R.; Lash, B. W.; King, M. R. Platelet Mediated TRAIL Delivery for Efficiently Targeting Circulating Tumor Cells. Nanoscale Adv. 2020, 2, 3942-3953.
Perica, K.; Tu, A.; Richter, A.; Bieler, J. G.; Edidin, M.; Schneck, J. P. Magnetic Field-Induced T Cell Receptor Clustering by Nanoparticles Enhances T Cell Activation and Stimulates Antitumor Activity. ACS Nano 2014, 8, 2252-2260.
Rabanel, J.-M.; Adibnia, V.; Tehrani, S. F.; Sanche, S.; Hildgen, P.; Banquy, X.; Ramassamy, C. Nanoparticle Heterogeneity: An Emerging Structural Parameter Influencing Particle Fate in Biological Media? Nanoscale 2019, 11, 383-406.
Reis, C. R.; van der Sloot, A. M.; Natoni, A.; Szegezdi, E.; Setroikromo, R.; Meijer, M.; Sjollema, K.; Stricher, F.; Cool, R. H.; Samali, A.; Serrano, L.; Quax, W. J. Rapid and Efficient Cancer Cell Killing Mediated by High-Affinity Death Receptor Homotrimerizing TRAIL Variants. Cell Death Dis. 2010, 1, e83-e83.
Reuter, K. G.; Perry, J. L.; Kim, D.; Luft, J. C.; Liu, R.; DeSimone, J. M. Targeted PRINT Hydrogels: The Role of Nanoparticle Size and Ligand Density on Cell Association, Biodistribution, and Tumor Accumulation. Nano Lett. 2015, 15, 6371-6378.

(56) References Cited

OTHER PUBLICATIONS

Rideau, E.; Dimova, R.; Schwille, P.; Wurm, F. R.; Landfester, K. Liposomes and Polymersomes: A Comparative Review towards Cell Mimicking. Chem. Soc. Rev. 2018, 47, 8572-8610.
Rideau, E.; Wurm, F. R.; Landfester, K. Membrane Engineering: Phase Separation in Polymeric Giant Vesicles. Small 2020, 16, 1905230.
Rinaldin, M.; Fonda, P.; Giomi, L.; Kraft, D. J. Geometric Pinning and Antimixing in Scaffolded Lipid Vesicles. Nat. Commun. 2020, 11, 4314.
Rosetti, C. M.; Mangiarotti, A.; Wilke, N. Sizes of Lipid Domains: What Do We Know from Artificial Lipid Membranes? What Are the Possible Shared Features with Membrane Rafts in Cells? Biochim. Biophys. Acta—Biomembr. 2017, 1859, 789-802.
Sanchez, L.; Yi, Y.; Yu, Y. Effect of Partial PEGylation on Particle Uptake by Macrophages. Nanoscale 2017, 9, 288-297.
Schindelin, J.; Arganda-Carreras, I.; Frise, E.; Kaynig, V.; Longair, M.; Pietzsch, T.; Preibisch, S.; Rueden, C.; Saalfeld, S.; Schmid, B.; Tinevez, J.-Y.; White, D. J.; Hartenstein, V.; Eliceiri, K.; Tomancak, P.; Cardona, A. Fiji: An Open-Source Platform for Biological-Image Analysis. Nat. Methods 2012, 9, 676-682.
Sezgin, E.; Levental, I.; Mayor, S.; Eggeling, C. The Mystery of Membrane Organization: Composition, Regulation and Roles of Lipid Rafts. Nat. Rev. Mol. Cell Biol. 2017, 18, 361-374.
Shishina, A. K.; Kovrigina, E. A.; Galiakhmetov, A. R.; Rathore, R.; Kovrigin, E. L. Study of Förster Resonance Energy Transfer to Lipid Domain Markers Ascertains Partitioning of Semisynthetic Lipidated N-Ras in Lipid Raft Nanodomains. Biochemistry 2018, 57, 872-881.
Smith, M. R.; Tolbert, S. V.; Wen, F. Protein-Scaffold Directed Nanoscale Assembly of T Cell Ligands: Artificial Antigen Presentation with Defined Valency, Density, and Ratio. ACS Synth. Biol. 2018, 7, 1629-1639.
Spitzer, D.; McDunn, J. E.; Plambeck-Suess, S.; Goedegebuure, P. S.; Hotchkiss, R. S.; Hawkins, W. G. A Genetically Encoded Multifunctional Trail Trimer Facilitates Cell-Specific Targeting and Tumor Cell Killing. Mol. Cancer Ther. 2010, 9, 2142-2151.
Trementozzi, A. N.; Imam, Z. I.; Mendicino, M.; Hayden, C. C.; Stachowiak, J. C. Liposome-Mediated Chemotherapeutic Delivery Is Synergistically Enhanced by Ternary Lipid Compositions and Cationic Lipids. Langmuir 2019, acs.langmuir.9b01965.
Veatch, S. L.; Keller, S. L. Separation of Liquid Phases in Giant Vesicles of Ternary Mixtures of Phospholipids and Cholesterol. Biophys. J. 2003, 85, 3074-3083.
Von Karstedt, S.; Montinaro, A.; Walczak, H. Exploring the TRAILs Less Travelled: TRAIL in Cancer Biology and Therapy. Nat. Rev. Cancer 2017, 17, 352-366.

* cited by examiner

PHASE-SEGREGATED VESICLES FOR SPATIALLY CONTROLLED PROTEIN-CONJUGATION AND CELL THERAPY

CROSS-REFERENCE TO RELATED APPLICATIONS

This application claims priority to U.S. Provisional Application No. 63/202,121 filed on May 27, 2021, the contents of which are incorporated by reference in their entireties.

STATEMENT REGARDING FEDERALLY SPONSORED RESEARCH

This invention was made with government support under grant number 1844219 and 1844336 awarded by the National Science Foundation. The government has certain rights in this invention.

BACKGROUND

The spatial presentation of ligands has a critical impact on cellular response. The density and inter-ligand distance of extracellular ligands interacting with their receptors can control binding and adhesion, ultimately affecting cell signaling pathways and controlling a range of processes from immune responses to stem cell differentiation.[1-3] For ligand-conjugated, therapeutic nanoparticles, the ligand density and spacing can affect cellular binding and uptake and receptor activation.[4-5] By considering the role of ligand spatial presentation, therapeutic nanoparticles may be better designed to elicit desired cellular responses. Towards this goal, Janus nanoparticles, particles with two unique surfaces with distinct properties, have been developed to control the location and density of surface-conjugated ligands. Janus nanoparticles allow precise patterning of ligands on opposite faces, which have been used to study endocytosis of partial PEGylation,[6] ligand clustering for T cell activation,[7,8] and to develop nanoparticles that mimic antibodies.[9] Yet the assembly of these particles is difficult, requiring complex chemistry and manufacturing schemes, hindering their adoption as therapeutic nanoparticles despite their unique advantages.

Accordingly, there remains a need in the art for improved nanoparticles for delivering therapeutics that are easy to produce in large quantities.

SUMMARY

In a first aspect, the present invention provides compositions comprising phase separated nanoparticles comprising: one or more unsaturated lipid, one or more saturated lipid, cholesterol, and a therapeutic agent.

In a second aspect, the present invention provides methods of making phase separated nanoparticles. The methods comprise (a) phase separating a lipid mixture comprising one or more unsaturated lipid, one or more saturated lipid, and cholesterol at a temperature that is below the melting temperature ($T_m$) of the saturated lipid but above the $T_m$ of the unsaturated lipid. In some embodiments, these methods further comprise: (b) incubating the phase separated nanoparticles with a therapeutic agent comprising a tag that binds to the label on the labeled lipid, thereby forming nanoparticle-therapeutic agent conjugates; and (c) isolating the nanoparticle-therapeutic agent conjugates formed in step (b) from the non-conjugated nanoparticles.

In a third aspect, the present invention provides methods of treating a subject having a tumor. The methods comprise: administering a therapeutically effective amount of a composition disclosed herein to treat the tumor.

DETAILED DESCRIPTION

Figure 1:
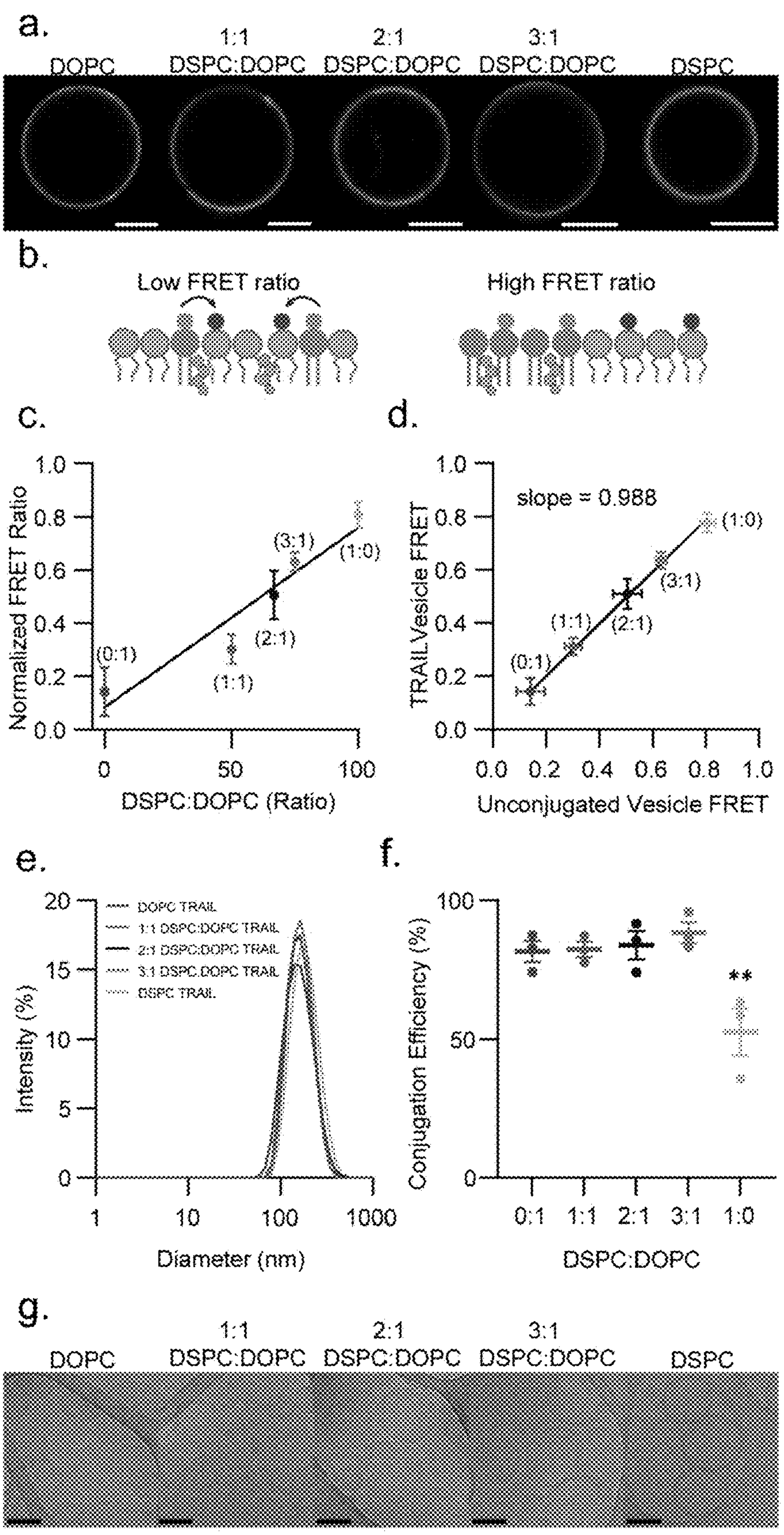
FIG. 1. Characterization of TRAIL conjugation to lipid domain vesicles. (a) Microscopy images of GUVs show phase separation of saturated lipids (light grey) and unsaturated lipids (red dark grey). Scale bars is 10 μm. (b) Schematic of a FRET assay to determine lipid domain presence in vesicles. (c) FRET analysis of vesicle lipid domains before TRAIL conjugation, where increasing FRET Ratio indicates the presence of domains. FRET ratio is reported as Fdonor/Facceptor. (d) FRET analysis of vesicle lipid domains before and after TRAIL conjugation shows no change after TRAIL conjugation. (e) Size distribution of TRAIL-conjugated vesicles measured by dynamic light scattering (DLS). (f) Conjugation efficiency of TRAIL to vesicles, as determined by western blot. Results were analyzed by ANOVA compared to 0:1 DSPC:DOPC as a control. ** $p<0.0001$, * $p<0.001$, ** $p<0.01$, *$p<0.05$. (g) Cryo-electron microscopy images of TRAIL vesicles. Scale bar=100 nm. Error bars represent SEM from n=3 different vesicle preparations (panels c-e and f).

The present invention provides compositions comprising phase separated nanoparticles, as well as methods of making the nanoparticles and uses thereof. The nanoparticles can be conjugated to therapeutics and used to treat diseases or to screen compounds.

The present application describes the generation of nanoparticles that comprise clusters of surface-conjugated molecules. Clustering improves the therapeutic efficacy of certain molecules. Thus, spatial control of surface-conjugated molecules is important for applications like drug delivery and can significantly improve the potency of certain nanoparticle-conjugated therapeutics. Thus non-homogenous lipid nanoparticles of the present invention have spatial patterns that enhance the effectiveness of the biomolecule, as described herein.

In the Examples, the inventors demonstrate that the biophysical properties of lipid membranes can be harnessed to spatially pattern therapeutic ligands on a nanoparticle surface. They show that clustering of the protein TNF-related apoptosis inducing ligand (TRAIL) on nanoparticles leads to more effective killing of cancer cells relative to when this protein is added in a soluble form or is homogenously distributed on the nanoparticle surface.

The nanoparticles of the present invention offer several advantages over the drug delivery methods of the prior art, including the simplicity of particle fabrication, ability of ligands to move/rearrange, ability to switch from Janus-like to non-Janus like particles, and ability to incorporate various membrane proteins into the nanoparticles. Importantly, because spatial patterning can enhance the potency of certain therapeutic agents, lower amounts of such agents need to be conjugated to the phase separated nanoparticles of the present invention to achieve the same therapeutic effect, which is economically advantageous. It is contemplated that different spatial patterns can be used (circles, stripes, etc.) which can provide different biological advantages in different systems. The changes in spatial patterns of domains to non-domains can be in creating switchable particles that turn off/on depending on the patterns it switches too. The change in spatial pattern should differentially engage target receptors leading to a commensurate change in cell signaling.

Compositions:

The present inventors discovered that molecules conjugated to the surface of nanoparticles can be spatially clustered via phase separation of lipids, and that this spatial patterning can improve the function of conjugated molecules. Thus, in a first aspect, the present invention provides compositions comprising phase separated nanoparticles comprising: one or more unsaturated lipid, one or more saturated lipid, cholesterol, and a therapeutic agent.

A “nanoparticle” is a small particle that ranges in size between about 1 to about 1000 nanometers. The nanoparticles of the present invention include vesicles (i.e., structures consisting of liquid enclosed by a lipid bilayer) made from a combination of lipids. In preferred embodiments, the nanoparticles are 30 nm to 200 μm in size. The nanoparticles may have any zeta potential (positive, negative, or neutral). Suitably, the lipid nanoparticles described herein are capable of phase separation, and thus allow for the spatial patterning of conjugated biomolecules on their surface.

“Phase separation” is a process by which a well-mixed solution of macromolecules (e.g., lipids, proteins, nucleic acids) spontaneously separates into two phases. In the nanoparticles of the present inventions, phase separation of lipids forms distinct regions (i.e., spatial patterns) on the nanoparticle surface. Specifically, the nanoparticles comprise (a) liquid-ordered ($L_o$) domains comprising saturated lipids and cholesterol, and (b) liquid-disordered ($L_d$) domains comprising unsaturated lipids. $L_d$ domains are characterized by more fluid diffusion and disordered packing of lipids, whereas $L_o$ domains are characterized by more ordered and tightly packed lipids. Phase separated $L_d$ and $L_o$ domains can be detected using fluorescent lipid probes, i.e., using a saturated lipid probe to stain $L_o$ and an unsaturated lipid to stain $L_d$. Notably, segregation into $L_d$ and $L_o$ domains mimics the formation of lipid rafts in a cell membrane.

Lipid phase separation is achieved by mixing one or more saturated lipid and one or more unsaturated lipid at an appropriate ratio. A suitable ratio for phase separation will depend on the particular lipids used in the nanoparticle. Examples of suitable rations include, without limitation, a 4:1, 3:1, 2:1, 1:1, 1:1.5, and 1:2 ratio of saturated lipid to unsaturated lipid. To allow for phase separation, the mixture is incubated at a temperature between the melting temperate ($T_m$) of the saturated and unsaturated lipids. Alternatively, phase separation can be achieved by varying the amount of cholesterol (or another sterol) in the lipid mixture. For example, omission of sterols will cause phase separation, but will lead to the formation of a solid phase.

"Cholesterol" is a waxy, fat-like substance made in the liver, and found in the blood and all cells of the body. It is a sterol (i.e., a modified steroid), a type of lipid. Cholesterol composes about 30% of all animal cell membranes. It is required to build and maintain membranes and modulates membrane fluidity over the range of physiological temperatures.

A "saturated lipid" is a lipid in which the fatty acid chains have all single bonds and are, thus, saturated with hydrogen molecules, whereas an "unsaturated lipid" is a lipid that contains one or more double bonds or triple bonds. Suitable saturated lipids that can be used in the nanoparticles of the present invention include, without limitation, 1,2-distearoyl-sn-glycero-3-phosphocholine (DSPC), dipalmitoylphosphatidylcholine (DPPC), 1,2-distearoyl-sn-glycero-3-phospho-L-serine (DSPS), 1,2-dipalmitoyl-sn-glycero-3-phosphoserine (DPPS), 1,2-stearoyl-3-trimethylammonium-propane (DSTAP), 1,2-dipalmitoyl-sn-glycero-3-phosphoglycerol (DPPG), 1,2-distearoyl-sn-glycero-3-phosphoglycerol (DSPG), dipalmitoylphosphatidic acid (DPPA), and 1,2-distearoyl-sn-glycero-3-phosphate (DSPA). Suitable unsaturated lipids for use in the nanoparticles include, without limitation, 1,2-dioleoyl-sn-glycero-3-phosphocholine (DOPC), L-α-dioleoylphosphatidyl ethanolamine (DOPE), 1,2-dioleoyl-sn-glycero-3-phospho-L-serine (DOPS), 1,2-dioleoyl-3-trimethylammonium-propane (DOTAP), 1,2-Dioleoyl-sn-glycero-3-phosphoglycerol (DOPG), and dioleoylphosphatidic acid (DOPA). In specific embodiments, the one or more unsaturated lipid comprises DOPC and the one or more saturated lipid comprises DSPC. Any of the lipids used in the nanoparticles may comprise modifications. For example, the lipids may be conjugated to a fluorophore, polymer, or therapeutic agent, as discussed in the following paragraphs.

In some embodiments, the nanoparticles comprise a lipid that is modified to be conjugated to a fluorescent molecule to facilitate detection. In the Examples, the inventors included the unsaturated fluorophore-modified lipid 1,2-dioleoyl-sn-glycero-3-phosphoethanolamine-N-(lissamine rhodamine B sulfonyl) (18:1 Rho) and the saturated fluorophore-modified lipid 1,2-dipalmitoyl-sn-glycero-3-phosphoethanolamine-N-(7-nitro-2-1,3-benzoxadiazol-4-yl) (16:0 NBD) in their nanoparticles to allow them to track the spatial patterning of unsaturated and saturated lipids on the nanoparticle surface via fluorescent imaging. Thus, in some embodiments, the nanoparticles comprise 18:1 Rho and/or 16:0 NBD. Other suitable fluorophore-modified lipids for use in the nanoparticles include, without limitation, 1,2-dioleoyl-sn-glycero-3-phosphoethanolamine-N-(Cyanine 5.5) (18:1 Cy5.5 PE), 1,2-distearoyl-sn-glycero-3-phosphoethanolamine-N-(Cyanine 5.5) (18:0 Cy5.5 PE), 1,2-dioleoyl-sn-glycero-3-phosphoethanolamine-N-(Cyanine 7) (18:1 Cy7 PE), and 1,2-distearoyl-sn-glycero-3-phosphoethanolamine-N-(Cyanine 7) (18:0 Cy7 PE). Suitable fluorescent molecules that can be conjugated to lipids for use in the present compositions include, without limitation, fluorescein, fluorescein isothiocyanate, rhodamine, dichlorot[pi]azinylamine fluorescein, green fluorescent protein (GFP), red fluorescent protein (RFP), blue fluorescent dyes excited at wavelengths in the ultraviolet (UV) part of the spectrum (e.g., AMCA (7-amino-4-methylcoumarin-3-acetic acid); Alexa Fluor 350), green fluorescent dyes excited by blue light (e.g., FITC, Cy2, Alexa Fluor 488), red fluorescent dyes excited by green light (e.g., rhodamines, Texas Red, Cy3, Alexa Fluor dyes 546, 564 and 594), or dyes excited with infrared light (e.g., Cy5), dansyl chloride, and phycoerythrin.

In some embodiments, the nanoparticles comprise a lipid that is modified to be conjugated to a polymer. In the Examples, the inventors included lipids conjugated to polyethylene glycol (PEG) in their nanoparticles because this polymer is known to stabilize vesicles. Specifically, the inventors included the saturated PEG-modified lipid 1,2-distearoyl-sn-glycero-3-phosphoethanolamine-N-[methoxy(polyethylene glycol)-2000] (18:0 PEG2000-PE) in their nanoparticles. Thus, in some embodiments, the nanoparticles comprise 18:0 PEG2000-PE. Other suitable PEG-modified lipids for use in the nanoparticles include, without limitation, 1,2-dioleoyl-sn-glycero-3-phosphoethanolamine-N-[methoxy(polyethylene glycol)-2000] (18:1 PEG2000 PE), 1,2-distearoyl-sn-glycero-3-phosphoethanolamine-N-[methoxy(polyethylene glycol)-1000] (18:0 PEG1000 PE), 1,2-dioleoyl-sn-glycero-3-phosphoethanolamine-N-[methoxy(polyethylene glycol)-1000] (18:1 PEG1000 PE), 1,2-distearoyl-sn-glycero-3-phosphoethanolamine-N-[methoxy(polyethylene glycol)-500] (18:0 PEG500 PE), 1,2-dioleoyl-sn-glycero-3-phosphoethanolamine-N-[methoxy(polyethylene glycol)-500] (18:1 PEG500 PE), 1,2-distearoyl-sn-glycero-3-phosphoethanolamine-N-[methoxy(polyethylene glycol)-5000] (18:0 PEG5000 PE), and 1,2-dioleoyl-sn-glycero-3-phosphoethanolamine-N-[methoxy(polyethylene glycol)-5000] (18:1 PEG5000 PE).

In some embodiments, the nanoparticles comprise a lipid that is modified to comprise a label to which a tagged therapeutic agent can be conjugated. In the Examples, the inventors included lipids conjugated to a nickel label in their nanoparticles to allow for conjugation to a His-tagged protein via a His tag-nickel interaction. Specifically, the inventors included the unsaturated nickel-modified lipid 1,2-dioleoyl-sn-glycero-3-[(N-(5-amino-1-carboxypentyl) iminodiacetic acid)succinyl] (nickel salt) (DGS-NTA-Ni) in their nanoparticles. Thus, in some embodiments, the nanoparticles comprise DGS-NTA-Ni. Other suitable labels for drug conjugation include, without limitation, amines, thiols, maleimides, dibenzocyclooctyne (DBCO) groups, N-hydroxysuccinimide (NHS) groups, azides, SnapTags, HaloTags, and the like. The label may be linked directly to the headgroup of a lipid or may be linked indirectly via a linker (e.g., a PEG linker).

As used herein, the term "therapeutic agent" refers to a substance that has a therapeutic function. Exemplary therapeutic agents include, without limitation, pharmaceuticals, biologics, toxins, fragments of toxins, alkylating agents, enzymes, antibody/protein mimetics, antibiotics, antimetabolites, antiproliferative agents, chemotherapeutic agents, hormones, neurotransmitters, DNA, RNA, siRNA, oligonucleotides, antisense RNA, aptamers, lectins, compounds that alter cell membrane permeability, photochemical compounds, small molecules, liposomes, micelles, gene therapy vectors, viral vectors, immunological therapeutic constructs, and other drugs.

In some embodiments, the therapeutic agent is a protein. The terms "polypeptide," "protein," and "peptide" are used interchangeably herein to refer to a series of amino acid residues connected by peptide bonds between the alpha-amino and carboxy groups of adjacent residues, forming a polymer of amino acids. Polypeptides may include modified amino acids. Suitable polypeptide modifications include, but are not limited to, acylation, acetylation, formylation, lipoylation, myristoylation, palmitoylation, alkylation, isoprenylation, prenylation, amidation at C-terminus, glycosylation, glycation, polysialylation, glypiation, and phosphorylation. Polypeptides may also include amino acid analogs.

In some embodiments, the therapeutic agent is an immune modulatory protein or a cancer-targeting protein. As used herein, an "immune modulatory protein" is a protein that acts on or takes part in a pathway that affects immune system function. Suitable immune modulatory proteins include, without limitation, immunostimulatory proteins (e.g., anti-CD3 antibodies, anti-CD28 antibodies), checkpoint inhibitors (e.g., anti-PD1 antibodies, anti-PDL1 antibodies), and anticoagulant proteins. As used herein, a "cancer-targeting protein" is a protein that acts on or takes part in a pathway that affects cancer growth or survival. Suitable cancer-targeting proteins include, for example, members of the tumor necrosis factor (TNF) family, such as TNF-related apoptosis inducing ligand (TRAIL), which is known to induce apoptosis in cancer cells but not normal cells.

In the Examples, the inventors incorporated a His-tagged therapeutic agent (i.e., TRAIL) into their phase separated nanoparticles via binding to a nickel-conjugated lipid (DGS-NTA-Ni). Thus, in some embodiments, the therapeutic agent is conjugated to one or more lipids on the nanoparticle.

Methods of Making Phase Separated Nanoparticles:

In a second aspect, the present invention provides methods of making phase separated nanoparticles. The methods comprise (a) phase separating a lipid mixture comprising one or more unsaturated lipid, one or more saturated lipid, and cholesterol at a temperature that is below the melting temperature ($T_m$) of the saturated lipid but above the $T_m$ of the unsaturated lipid.

In some examples, lipids should be mixed at appropriate temperature above the phase transition temperature of the saturated lipid component and then cooled to room temperature, which should lead to phase segregation. Vesicles can also be made separately (an unsaturated vesicle and a saturated vesicle) and then fused together via fusion methods (e.g., charge, DNA, etc.) to make phase-separated vesicles.

In some embodiments, the lipid mixture includes a labeled lipid that comprises a label. As used herein, the term "label" refers to a moiety that is specifically bound by a tag, and a "tag" is a moiety that specifically binds to a label. This allows for the direct conjugation of the lipid comprising the label to be bound to any therapeutic moiety displaying a tag. Examples of suitable tag/label pairs include, without limitation, His tag/nickel, GST tag/glutathione, cMyc/cMyc monoclonal antibody, flag tag/anti-flag monoclonal antibody, biotin/streptavidin, and the like. In preferred embodiments, the tag is a His tag and the label is nickel. In some embodiments, the labeled lipid is DGS-NTA and the label is nickel.

In the Examples, the inventors incorporated a His-tagged therapeutic agent into their phase separated nanoparticles via conjugation to a nickel-labeled lipid (DGS-NTA-Ni). Thus, in some embodiments, the methods further comprise: (b) incubating the phase separated nanoparticles with a therapeutic agent comprising a tag that binds to the label on the labeled lipid, thereby forming nanoparticle-therapeutic agent conjugates; and (c) isolating the nanoparticle-therapeutic agent conjugates formed in step (b) from the non-conjugated nanoparticles. Isolation of the nanoparticle-therapeutic agent conjugates may be accomplished using various purification methods known in the art including, without limitation, size exclusion chromatography, dialysis, flow filtration, affinity chromatography, and microfluidic-based methods.

In some embodiments, step (a) of the method comprises mixing: (i) one or more saturated lipid, (ii) one or more unsaturated lipid, and (iii) cholesterol. In these embodiments, the lipids are mixed at a ratio that allows for phase separation of liquid-ordered ($L_o$) and liquid-disordered ($L_d$) domains. A suitable ratio for phase separation will depend on the particular lipids used in the nanoparticle. Examples of suitable rations include, without limitation, a 4:1, 3:1, 2:1, 1:1, 1:1.5, and 1:2 ratio of saturated lipid to unsaturated lipid.

The present invention also provides nanoparticles made by the methods disclosed herein.

Methods of Treating Tumors:

In a third aspect, the present invention provides methods of treating a subject having a tumor. The methods comprise: administering a therapeutically effective amount of a nanoparticle composition disclosed herein to treat the tumor.

As used herein the term "tumor" refers to an abnormal mass of tissue in which the growth of the mass surpasses and is not coordinated with the growth of normal tissue. In the case of hematological cancers, this includes a volume of blood or other bodily fluid containing cancerous cells. The tumors treated using the methods of the present invention can be of any cancer type including, but not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma and peripheral neuroepithelioma.

As used herein, "treating" describes the management and care of a subject for the purpose of combating a disease, condition, or disorder. Treating includes administering a treatment to prevent the onset of the symptoms or complications, to alleviate the symptoms or complications, or to eliminate the disease, condition, or disorder. For example, treating cancer in a subject includes the reducing, repressing, delaying, or preventing of cancer growth, reduction of tumor volume, and/or preventing, repressing, delaying, or reducing metastasis of the tumor. Treating cancer in a subject also includes the reduction of the number of tumor cells within the subject.

As used herein, the term "administering" refers to the introduction of a substance into a subject's body. Methods of administration are well known in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, intradermal administration, intrathecal administration, and subcutaneous administration. Administration can be continuous or intermittent. In preferred embodiments, the composition is administered intravenously or intratumorally.

The term "therapeutically effective amount" refers to an amount sufficient to effect beneficial or desirable biological or clinical results. That result can be reducing, alleviating, inhibiting, or preventing one or more symptoms of a disease or condition, reducing, inhibiting, or preventing the growth of cancer cells, reducing, inhibiting, or preventing metastasis of the cancer cells or invasiveness of the cancer cells or metastasis, or reducing, alleviating, inhibiting, or preventing one or more symptoms of the cancer or metastasis thereof, or any other desired alteration of a biological system. In some embodiments, the effective amount is an amount suitable to provide an anti-tumor response. An anti-tumor response may be demonstrated, for example, by a decrease in tumor size or an increase in immune cell activation (e.g., CD8+ T cell activation). For any active agent, a therapeutically effective amount can be estimated initially in cell culture assays or in animal models, usually mice, rabbits, dogs, or pigs. An animal model may also be used to determine a desirable concentration range and route of administration. Methods for determining an effective means of administration and dosage are well known to those of skill in the art and will vary with the formulation used for therapy, the purpose of the therapy, the target cell being treated, and the subject being treated. Single or multiple administrations can be carried out with the dose level and pattern being selected by the treating physician.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

In the following example, the inventors generate a composition in which phase separated nanoparticles are used as carriers for proteins, and they demonstrate the easy assembly and enhanced anti-tumor properties of these nanoparticles. Specifically, the inventors harness lipid phase separation to spatially control protein presentation on lipid vesicles. They use this system to improve the cytotoxicity of TNF-related apoptosis inducing ligand (TRAIL), a therapeutic anti-cancer protein. Vesicles with phase-separated TRAIL presentation induced more cell death in Jurkat cancer cells than vesicles with uniformly conjugated TRAIL, and cytotoxicity was dependent on the TRAIL domain density. They then assessed this relationship in other cancer cell lines and demonstrated that phase-separated vesicles with TRAIL only enhanced cytotoxicity through one TRAIL receptor, DR5, while another TRAIL receptor, DR4, was unaffected by the TRAIL density. This work provides a rapid and accessible method for controlling protein conjugation and density on vesicles that can be adopted to other nanoparticle systems to improve receptor signaling induction.

Background

The spatial presentation of ligands has a critical impact on cellular response. The density and inter-ligand distance of extracellular ligands interacting with their receptors can control binding and adhesion, ultimately affecting cell signaling pathways and controlling a range of processes from immune responses to stem cell differentiation.[1-3] For ligand-conjugated, therapeutic nanoparticles, the ligand density and spacing can affect cellular binding and uptake and receptor activation.[4,5] By considering the role of ligand spatial presentation, therapeutic nanoparticles may be better designed to elicit desired cellular responses. Towards this goal, Janus nanoparticles, particles with two unique surfaces with distinct properties, have been developed to control the location and density of surface-conjugated ligands. Janus nanoparticles allow precise patterning of ligands on opposite faces, which have been used to study endocytosis of partial PEGylation,[6] ligand clustering for T cell activation,[7,8] and to develop nanoparticles that mimic antibodies.[9] Yet the assembly of these particles is difficult, requiring complex chemistry and manufacturing schemes, hindering their adoption as therapeutic nanoparticles despite their unique advantages.

In contrast to nanoparticles, cellular membranes naturally control the spatial presentation of ligands using phase-segregated lipid rafts. Lipid rafts are compartmentalized regions on the cell membrane characterized by increased cholesterol and saturated lipid content. These structures segregate distinct populations of biomolecules, affecting local membrane properties, lipid-protein interactions, and protein signaling.[10] Phase separation can be readily replicated in synthetic, self-assembled lipid systems.[11] Phospholipid bilayers, both in planar and nanoparticle form, can undergo phase separation when the appropriate mixtures of membrane components are used.[12,13] Beyond a limited number of examples,[14,15] this rich physical phenomenon has rarely been exploited to better design therapeutic nanoparticles.

A therapeutic target that could benefit from controlled presentation of ligands on a nanoparticle surface is the death receptor apoptosis pathway for anti-cancer therapy. In this pathway, TNF-related apoptosis inducing ligand (TRAIL), a homotrimer, binds to death receptors DR4 and DR5 upregulated in cancer cells and induces apoptosis.[16] As TRAIL exhibits enhanced activity during oligomerization, recombinant TRAIL often requires further clustering or cross-linking for therapeutic use.[17] For example, TRAIL signaling has been shown to improve when conjugated onto a lipid vesicle (liposome) compared to soluble TRAIL.[18-20] This improvement is attributed to vesicle-promoted TRAIL oligomerization on the cell surface. Despite this improvement, TRAIL-conjugated vesicles still perform poorly in vivo, in part because we do not fully understand how TRAIL density impacts signaling. Methods that allow for greater control of TRAIL presentation should allow us to study TRAIL signaling and improve the anti-cancer activity of TRAIL-conjugated therapeutic nanoparticles.

Figure 5:
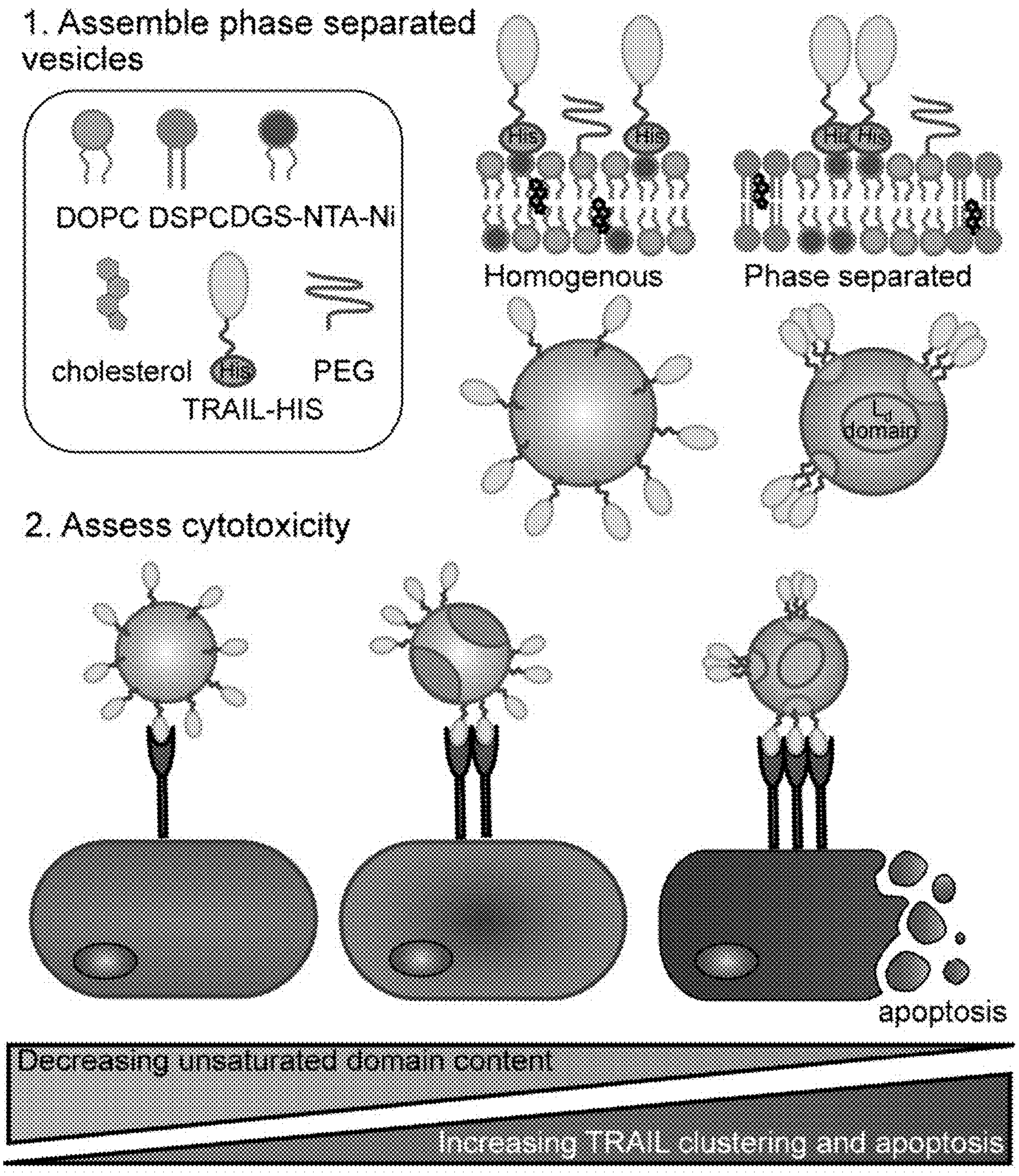
FIG. 5. Scheme 1. Design of TRAIL-conjugated nanoparticles using phase-separated lipid vesicles. (Top) By varying the ratio of unsaturated lipid (DOPC), saturated lipid (DSPC), and cholesterol, lipid vesicles can be assembled containing homogenous or phase segregated membranes. A nickel-conjugated lipid (DGS-NTA-Ni) that integrates into the liquid disordered phase of the membrane can bind histidine-tagged TRAIL proteins and generate nanoparticles with varying spatial densities of TRAIL. Nanoparticles with low unsaturated lipid content and increased density of TRAIL are hypothesized to enhance apoptosis in target cells.

We set out to test whether we could control TRAIL density through changes in lipid composition in vesicles, and whether the density of TRAIL could improve signaling and cancer cell apoptosis. By conjugating TRAIL to unsaturated lipids and varying the concentration of domain-forming saturated lipids, we reasoned that we could control TRAIL density in vesicles by decreasing the surface area available to TRAIL-conjugated lipids while keeping the concentration of TRAIL per nanoparticle constant overall. Furthermore, we hypothesized that TRAIL localization would improve receptor oligomerization on target cells and TRAIL-mediated signaling would increase, ultimately enhancing apoptosis. Using recombinant TRAIL, we show the extent to which lipid phase separation can be harnessed to change the spatial density of TRAIL on vesicle surfaces and increase TRAIL signaling. By leveraging the intrinsic ability of lipid vesicles to phase separate, we demonstrate that lipid composition can be engineered to modulate the spatial density of proteins on a vesicle surface and promote TRAIL clustering and cytotoxic efficacy (FIG. 5).

Results

To control the surface density of TRAIL on liposomes, we assembled nanovesicles with varying levels of membrane phase separation. DOPC (1,2-dioleoyl-sn-glycero-3-phosphocholine), an unsaturated lipid, forms a liquid-disordered (La) phase, whereas DSPC (1,2-distearoyl-sn-glycero-3-phosphocholine)/cholesterol mixtures form a liquid-ordered ($L_o$) phase.[21] When mixed at appropriate ratios, these three lipids can phase separate into $L_d$ and $L_o$ phases within a single vesicle membrane. Lipid vesicles were assembled using ternary mixtures of DOPC and DSPC at varying ratios with cholesterol at a constant 30 mol %. To localize TRAIL to select regions of the membrane, we included an unsaturated lipid with a Ni-NTA (nickel-nitrilotriacetic acid) headgroup that localized into La regions in the liposome membrane. This Ni-NTA lipid allowed conjugation of His-tagged TRAIL to our vesicles after vesicle formation. Polyethylene glycol (PEG, [18:0 PEG(2000)]), conjugated to a saturated lipid, was incorporated at 1 mol % for vesicle stability and should partition away from Ni-NTA lipids to reduce possible steric hindrance. Vesicles were extruded to 100 nm, an ideal size for drug delivery, incubated with His-tagged TRAIL, and dialyzed to remove unconjugated protein. By increasing the ratio of DSPC to DOPC in these vesicles, we expected to increase the size of $L_o$ domains and reduce the size of $L_d$ domains, respectively.

Figure 6:
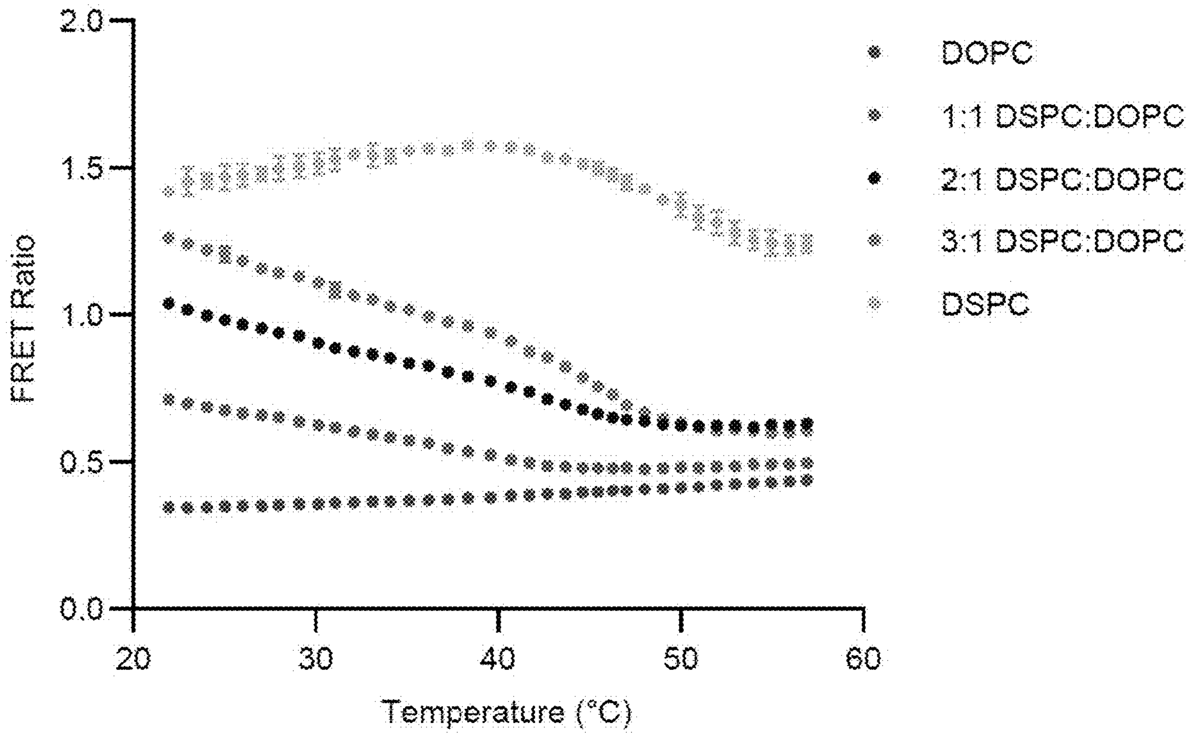
FIG. 6. Temperature dependence of lipid domains measured by FRET ratio. Error bars represent SEM from n=3 different vesicle preparations. Increasing temperatures lead to a convergence of FRET ratios for most lipid compositions, indicating FRET signals reflect membrane domains and temperature induced dissolution of domains leads to similar FRET signals.

We used microscopy and Förster resonance energy transfer (FRET) analysis to confirm lipid phase separation. Vesicles were labeled with a saturated lipid dye (16:0 NBD, [N-(7-Nitrobenz-2-Oxa-1,3-Diazol-4-yl)]) and an unsaturated lipid dye (18:1 Rho, [Lissamine-Rhodamine PE]) that should separate into $L_o$ and $L_d$ domains, respectively. Because we cannot visualize lipid domains in nanovesicles using microscopy, we created giant unilamellar vesicles (GUVs), micron-sized vesicles formed through electroformation with complementary properties to nanovesicles.[11] GUVs showed segregation of 16:0 NBD and 18:1 Rho into distinct regions of the membrane in ternary compositions of DOPC, DSPC and cholesterol, confirming the formation of phase-separated lipid domains (FIG. 1A). In compositions with only DOPC or DSPC and cholesterol, the two dyes did not segregate. Next, we measured the FRET efficiency between 16:0 NBD (donor) and 18:1 Rho (acceptor) to assess the spatial separation between $L_o$ and $L_d$ phases in nanovesicles that would be used for cell studies (FIG. 1B).[22,23] These studies demonstrated measurable differences in FRET ratio (here reported as normalized $F_{donor}/F_{acceptor}$; see Equation 1 and 2 in the Materials & Methods section, below) as a function of DSPC content, suggesting differences in phase separation as a function of vesicle composition (FIG. 1C). As expected, vesicles composed of DOPC alone showed the lowest FRET ratio, indicating the two fluorescent probes were more uniformly distributed across the membrane. Increases in the mole fraction of DSPC increased the FRET ratio, indicating the saturated and unsaturated lipids were located farther apart within a given membrane and suggesting the presence of nanodomains. Pure DSPC vesicles exhibited the highest FRET ratio, which we attribute to the presence of extremely small $L_d$ domains that result from segregation of the NTA-lipids and unsaturated lipid dye. Conjugation of TRAIL to DGS-NTA-Ni did not change vesicle FRET values, indicating the conjugation of TRAIL did not disrupt domains (FIG. 1D). To further confirm that the FRET data reflected the presence of membrane domains, we used a temperature ramp to destabilize domains.[11,22] Our temperature studies show that the FRET ratio is temperature-dependent and decreased at higher temperatures; this result is expected, as domains are known to dissolve and lipids become well mixed when approaching the melting temperature ($T_m$) of the saturated lipid (55° C. for DSPC, FIG. 6). In summary, our characterization of giant and nano-sized vesicles confirms that our choice of lipid mixtures yields vesicles with varied degrees of lipid segregation, that is conserved upon TRAIL conjugation.

Figure 7:
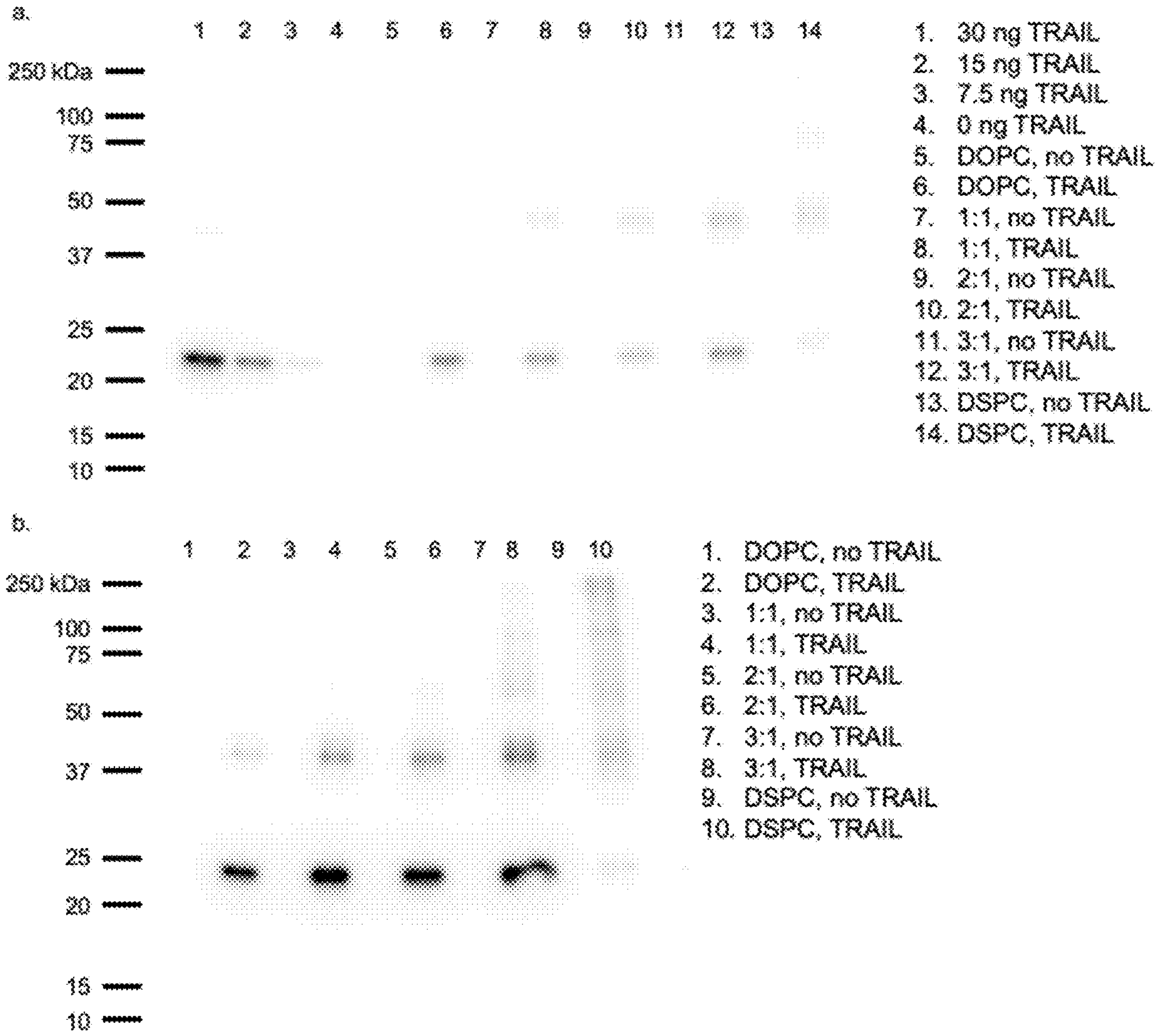
FIG. 7. Western blot of TRAIL conjugated vesicles. (a) Representative uncropped anti-TRAIL western blot of TRAIL-conjugated vesicles. Corresponding lane key is to the right of the blot and molecular weight markers are labeled in kDa to the left of the blot. A standard curve was generated using purified TRAIL (lanes 1-4) and used to calculate the concentration of TRAIL conjugated to vesicles by densitometry. (b) Representative anti-TRAIL western blot performed using non-reducing conditions of TRAIL labeled vesicles. Corresponding lane key is to the right of the blot and molecular weight markers are labeled in kDa to the left of the blot. As TRAIL becomes more concentrated in Ld domains, TRAIL forms more oligomeric structures, as seen on the blot.
Figure 8:
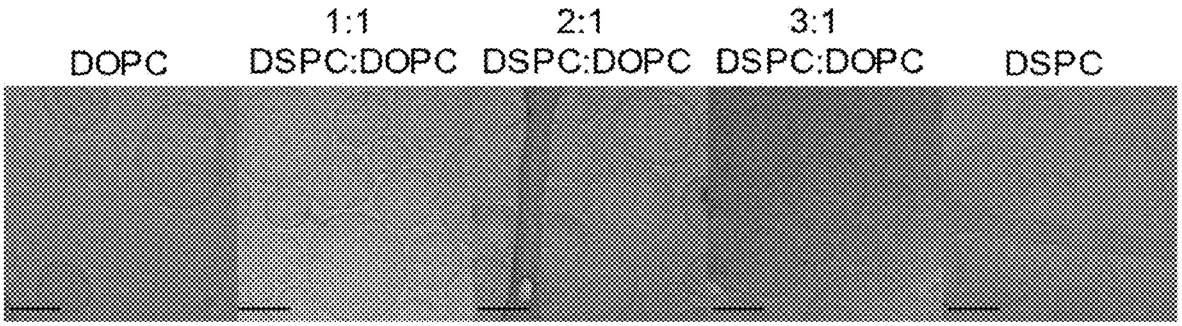
FIG. 8. Cryo-electron microscopy data of unconjugated vesicles. Scale bar=100 μm.

Next, we measured several physical and chemical properties of the TRAIL-conjugated vesicles. All TRAIL-conjugated vesicle compositions exhibited a similar size and zeta potential (FIG. 1E, Table 1, and Table 2). We next confirmed the extent of TRAIL conjugation onto the vesicles using western blot analysis. DOPC, 1:1 DSPC:DOPC, 2:1 DSPC:DOPC, and 3:1 DSPC:DOPC compositions all showed similar levels of TRAIL conjugation, while DSPC vesicles demonstrated less TRAIL conjugation (FIG. 1F and FIG. 7A). We hypothesize that TRAIL conjugation to DSPC vesicles is poor because DGS-NTA-Ni is unsaturated and assembles into extremely small $L_d$ domains. As a result, steric hindrance from conjugated TRAIL molecules could prevent other TRAIL molecules from associating with unoccupied/unbound DGS-NTA-Ni. Non-reducing western blot analysis revealed oligomeric TRAIL structures in vesicles that increased in number as the $L_o$ domain size decreased (FIG. 7B). DSPC vesicles exhibited extremely large oligomers, which supports our hypothesis that TRAIL-conjugated lipids are highly segregated in this region and likely to prevent other TRAIL molecules from binding to unbound DGS-NTA-Ni. Nonetheless, all other compositions showed similar levels of TRAIL conjugation. Finally, we imaged our nanovesicles using cryo-electron microscopy (cryo-EM) before and after TRAIL conjugation (FIG. 1G and FIG. 8) and observed no changes in morphology across all samples. We therefore established a series of membrane compositions that displayed differential phase separation but similar overall total TRAIL concentrations and morphologies, allowing us to isolate the role of TRAIL spatial density on cell cytotoxicity.

TABLE 1

Summary values of size, polydispersity (PDI), and Zeta potential of TRAIL-conjugated vesicles (n = 3 different vesicle preparations) as determined using dynamic light scattering.

| | Size (nm) | PDI | Zeta potential (mV) |
|---|---|---|---|
| DOPC | 165 ± 59 | 0.13 | −3.8 ± 1.2 |
| 1:1 DSPC:DOPC | 161 ± 52 | 0.10 | −4.4 ± 0.8 |
| 2:1 DSPC:DOPC | 170 ± 57 | 0.11 | −3.7 ± 0.9 |
| 3:1 DSPC:DOPC | 171 ± 51 | 0.09 | −4.0 ± 0.3 |
| DSPC | 191 ± 65 | 0.12 | −3.4 ± 0.9 |

TABLE 2

Nanoparticle tracking analysis (NTA) data of size and number of particles per 5 μM lipid vesicle concentration. Error represents n =3 reads from one sample.

| | Size (nm) | Number of particles (5 μM lipid) |
|---|---|---|
| DOPC | 131 ± 52 | $7.76e^8 \pm 9.48e^6$ particles/ml |
| 1:1 DSPC:DOPC | 129 ± 53 | $1.12e^9 \pm 2.03e^7$ particles/ml |
| 2:1 DSPC:DOPC | 118 ± 44 | $5.83e^8 \pm 4.20e^7$ particles/ml |
| 3:1 DSPC:DOPC | 140 ± 43 | $1.15e^9 \pm 5.99e^7$ particles/ml |
| DSPC | 152 ± 95 | $1.25e^9 \pm 6.99e^6$ particles/ml |

Figure 2:
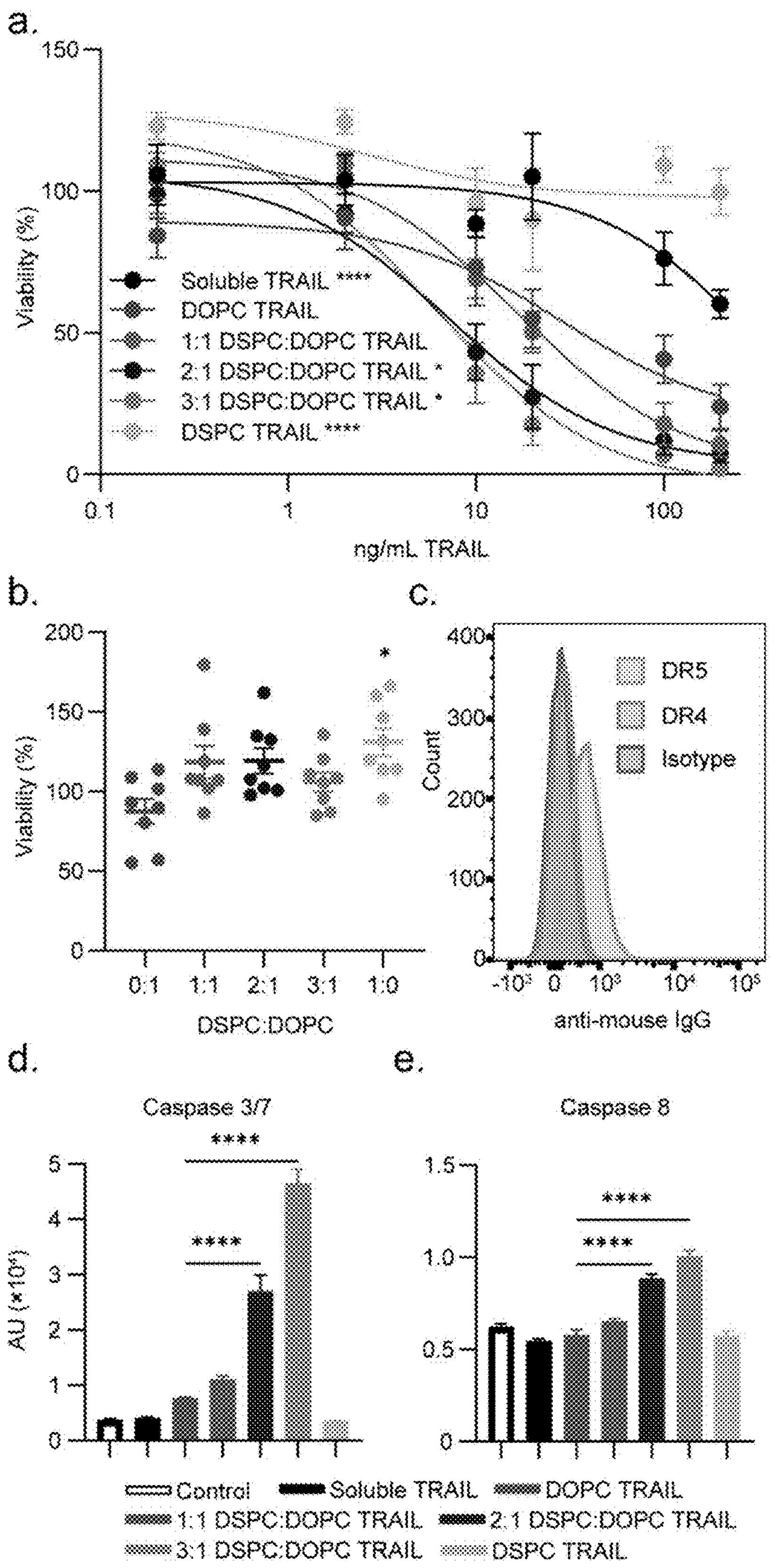
FIG. 2. Vesicle lipid domains enhance TRAIL activation in Jurkat cells. (a) Viability of Jurkat cells treated with different concentrations of soluble and vesicle TRAIL after 24 hours. Error bars represent SEM from n=6 using 2 different vesicle preparations. Concentration reported is the initial amount of TRAIL added to the vesicles during conjugation. Results were analyzed by two-way ANOVA with multiple comparisons compared to DOPC TRAIL. (b) Viability of Jurkat cells to 1 mM unconjugated lipid vesicles, which corresponds to the highest TRAIL-conjugated vesicle concentration tested. Error bars represent SEM from n=8 from 3 different vesicle preparations. p values reflect an ANOVA with multiple comparisons compared to untreated Jurkat cells. (c) Flow cytometry analysis of Jurkat expression of TRAIL receptors DR4 and DR5. (d,e) Activation of caspase 3/7 (d) and caspase 8 (e) in Jurkat cells exposed to soluble and vesicle TRAIL (20 nM) after 3 hours. Error bars represent SEM from n=3. p values were generated using ANOVA with multiple comparisons. **$p<0.0001$, *$p<0.001$, **$p<0.01$, *$p<0.05$.
Figure 3:
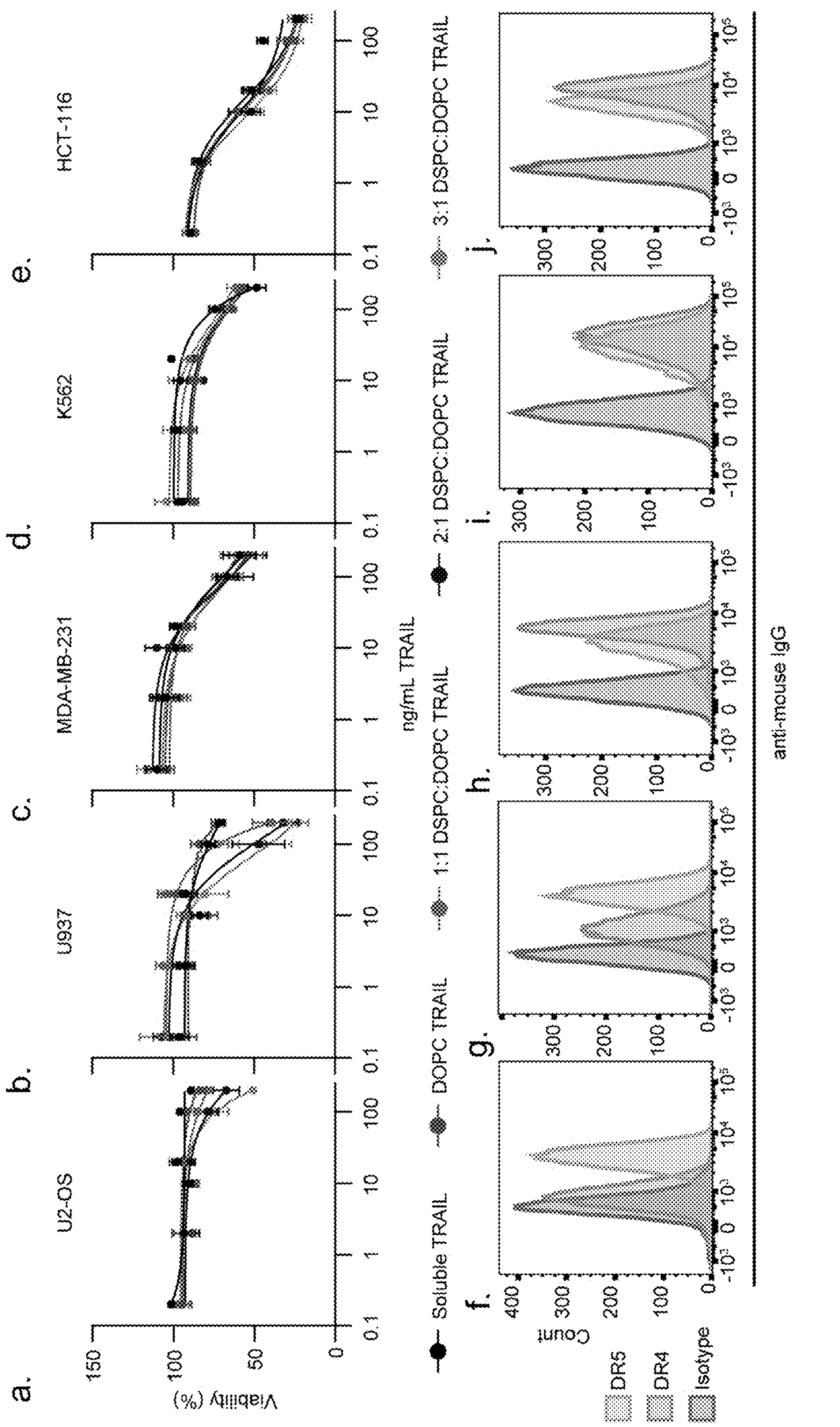
FIG. 3. Cytotoxicity of TRAIL conjugated to vesicles with lipid domains depends on cell type. Cell viability upon treatment with soluble and vesicle TRAIL after 24 hours and expression of TRAIL receptors DR4/DR5 of U2-OS (a,f), U937 (b,g), MDA-MB-231 (c,h), K562 (d,i) and HCT-116 (e,j). Error bars represent SEM from n=6 from two different vesicle preparations. Concentration reported is the initial amount of TRAIL added to the vesicles during conjugation. Only the 2:1 (*) and 3:1 (*) DSPC: DOPC TRAIL condition was statistically different from DOPC TRAIL for U2-OS and only the 3:1 DSPC: DOPC TRAIL condition was statistically different from DOPC TRAIL for U937 (*). Results were analyzed by two-way ANOVA with multiple comparisons compared to DOPC TRAIL as our control. *$p<0.05$.
Figure 9:
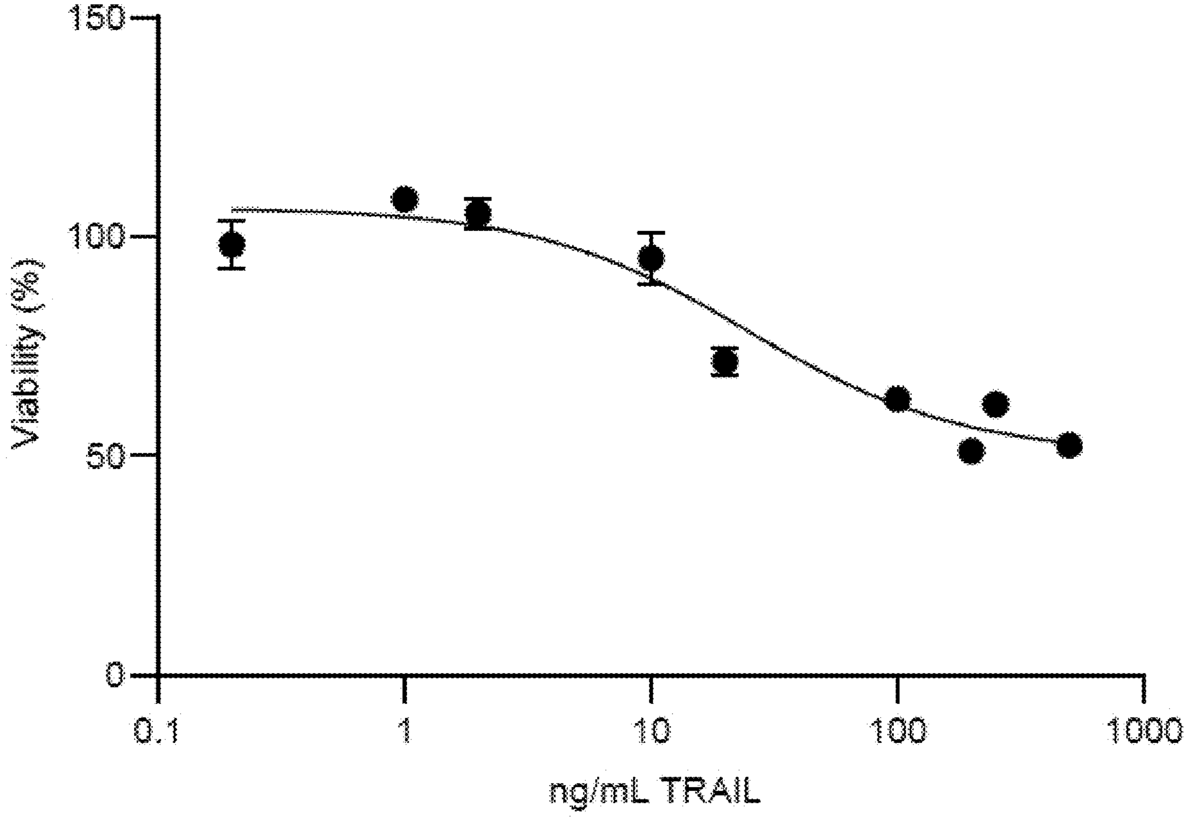
FIG. 9. Expanded viability study of soluble TRAIL up to 500 ng/mL. Soluble TRAIL plateaus at approximately 50% viability. Error bars represent SEM from n=3.
Figure 10:
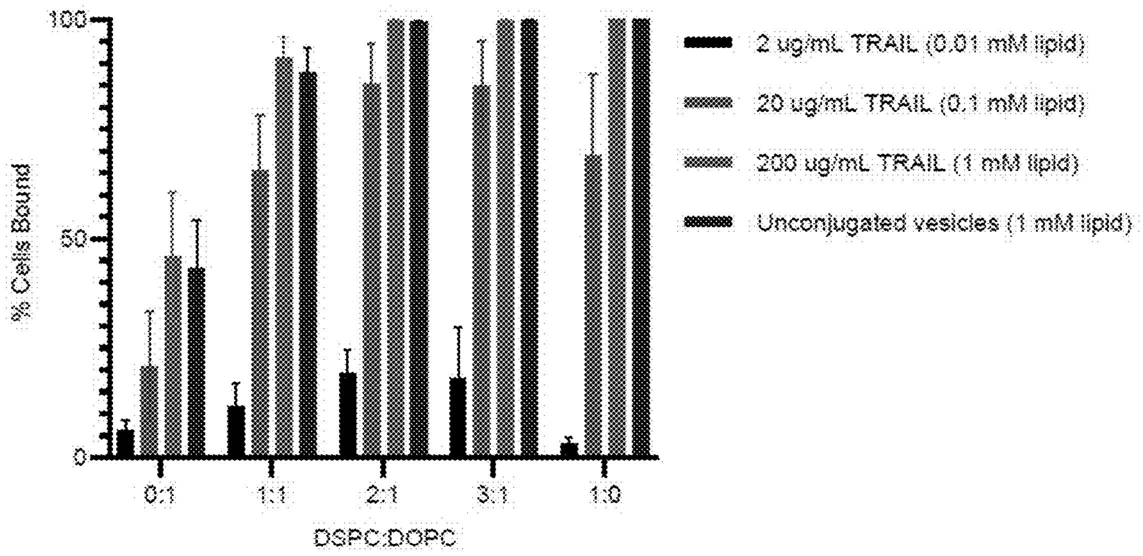
FIG. 10. Vesicle binding to Jurkat cells. Unconjugated vesicles are added at the same lipid concentration as 200 μg/mL TRAIL (1 mM lipid concentration) and vesicle binding is reported as both % cells bound and median fluorescence intensity (MFI). Error bars represent SEM from n=3 separate flow cytometry experiments with 3 vesicle preparations.
Figure 10:
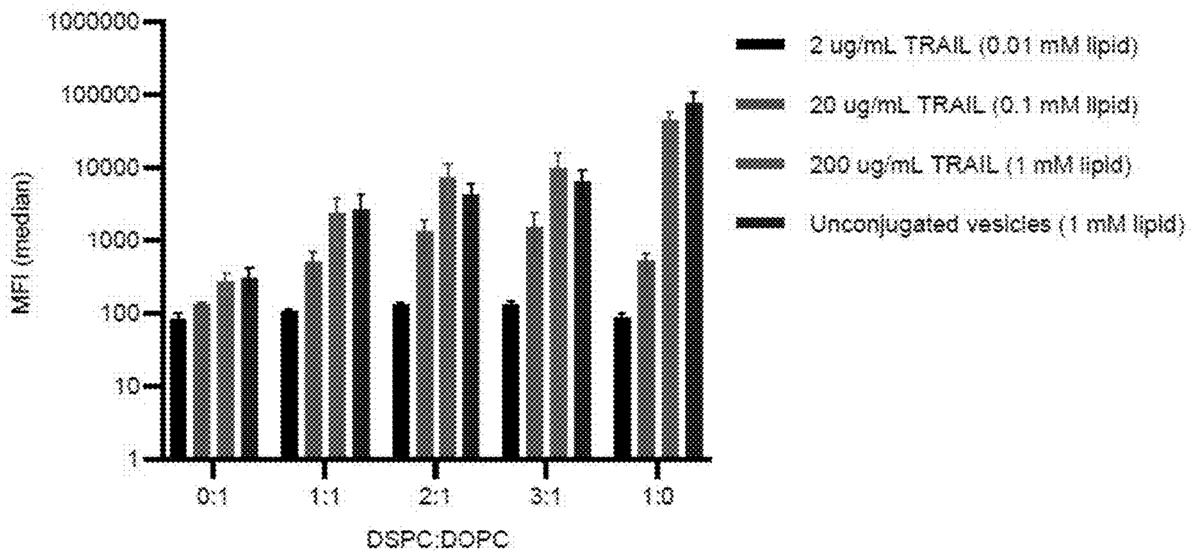
Figure 11:
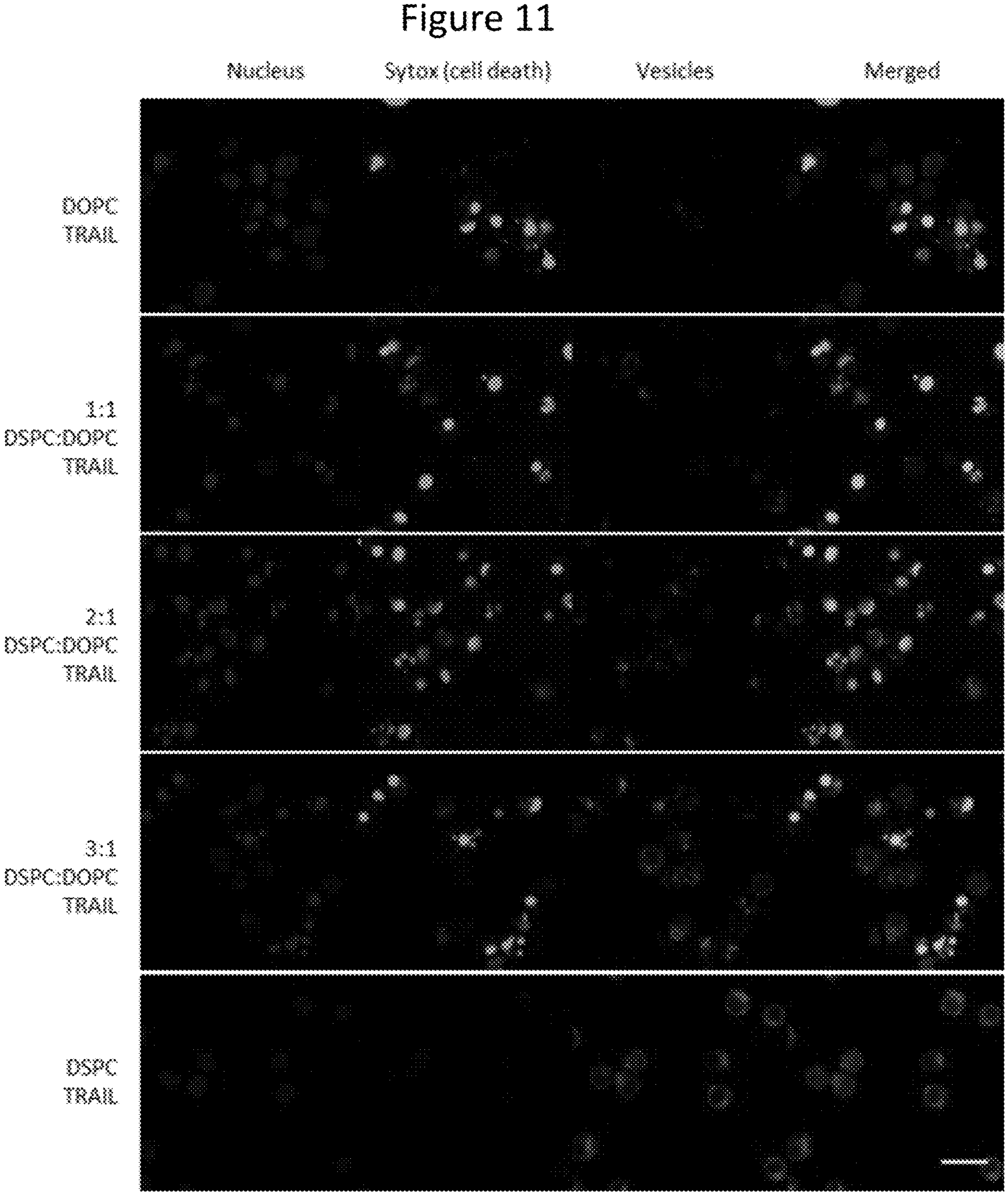
FIG. 11. Confocal microscopy images of TRAIL vesicles bound to Jurkat cells after 4 hours. Sytox green is used to stain dead cells, and vesicles are stained in red. Scale bar=20 μm.

We then studied the capacity of TRAIL-conjugated vesicles to initiate TRAIL-mediated apoptosis. To measure cytotoxicity of TRAIL-conjugated vesicles, we chose to first study Jurkat cells, which are more sensitive to TRAIL-conjugated vesicles than soluble TRAIL alone. This suggests Jurkat cells might be responsive to further spatial localization of TRAIL molecules within membrane domains.[20] Jurkat cells were treated with increasing concentrations of either soluble TRAIL or TRAIL-conjugated vesicles for 24 hours (FIG. 2A). Despite the fact that DOPC TRAIL and soluble TRAIL possess similar relative $IC_{50}$ values (29 ng/mL and 25 ng/mL, respectively), DOPC TRAIL vesicles were more efficacious, reducing viability to approximately 25% while the effect of soluble TRAIL plateaued at 50% even at higher concentrations (FIG. 9). Furthermore, we observed that segregation in vesicle domains increased the cytotoxicity of TRAIL and that cytotoxicity correlated with smaller domain size (3:1 DSPC:DOPC>2:1 DSPC:DOPC>1:1 DSPC:DOPC>DOPC). Decreasing the domain size both increased the efficacy, as domain-containing vesicles killed virtually all Jurkat cells at 200 ng/mL, and potency (relative $IC_{50}$ of 17 ng/mL for 1:1 DSPC:DOPC, 7 ng/mL for 2:1 DSPC:DOPC, and 6 ng/mL for 3:1 DSPC:DOPC). Surprisingly, DSPC vesicles did not exhibit any significant TRAIL-mediated cytotoxicity. While DSPC TRAIL vesicles had significantly less TRAIL conjugated on their surface, the concentration of TRAIL on DSPC vesicles should still have been sufficient to induce apoptosis and indicates some other feature of TRAIL presentation in these particles is likely affecting their efficacy. To rule out the possibility that the cytotoxic effects we observed were due to the lipid vesicles themselves, we treated Jurkat cells with unconjugated vesicles at the highest lipid concentration (1 mM lipid) used (FIG. 2B). As expected, Jurkat viability was not negatively affected by unconjugated vesicles. Flow cytometry analysis of TRAIL receptors showed Jurkat cells only expressed DR5 relative to DR4 (FIG. 2C). Binding studies of the vesicles to Jurkat cells demonstrated that increasing DSPC vesicle concentration increased binding of vesicles to cells nonspecifically, and that binding did not fully correlate with TRAIL-mediated cytotoxicity (FIG. 10 and FIG. 11). We hypothesize that the reduced cytotoxicity of DSPC-TRAIL vesicles may be due to the increased rigidity of DSPC vesicles or an altered presentation of TRAIL molecules on the surface of DSPC vesicles. This is supported by previous studies that demonstrated membrane fluidity affected immunoliposome binding towards target cells.[24,25] Our other vesicle compositions that showed robust TRAIL activity contained more unsaturated lipids and correspondingly more fluid membranes. Altogether, these results indicate that clustering TRAIL within $L_d$ domains of lipid vesicles increases cell signaling and apoptosis.

To further confirm TRAIL-mediated cell death, we next investigated the activation of intracellular apoptotic signaling molecules by monitoring caspase-3/7 and caspase-8 activity. When TRAIL binds to its receptors, death receptors 4 and 5 (DR4, DR5), it recruits FAS-associated protein with death domain (FADD) and pro-caspase-8 to the cell membrane. This leads to caspase-8 activation and subsequent caspase-3 and caspase-7 activation to induce apoptosis.[26] We therefore measured caspase-3/7 and caspase-8 activity to confirm cell death was the result of TRAIL-induced intracellular signaling. We measured caspase-3/7 and caspase 8 activity in Jurkat cells after 3 hours of incubation with vesicles containing 20 ng/mL of TRAIL. (FIGS. 2D and 2E, respectively). At this time point and concentration we saw minimal caspase activity from soluble TRAIL, DOPC TRAIL, 1:1 DSPC:DOPC TRAIL or DSPC TRAIL, but vesicles with smaller domains in the 2:1 DSPC:DOPC TRAIL and 3:1 DSPC:DOPC TRAIL compositions showed significantly increased caspase activity. Therefore, segregation of TRAIL in the $L_d$ domain of vesicles increased caspase 3/7 and caspase 8 activity after 3 hours over DOPC vesicles presenting uniformly distributed TRAIL. Curiously, DOPC TRAIL did not show any differences in caspase activity relative to soluble TRAIL at this time point despite increased cytotoxic activity over soluble TRAIL after 24 hours, which could indicate that clustering also affects the rate of caspase activity. Work studying Fas/FasL, which induces apoptosis similarly to TRAIL/DR5, demonstrated that the ligand spacing of FasL affected the apoptosis rate, which could explain increased caspase activity in the phase segregated 2:1 and 3:1 DSPC:DOPC TRAIL compositions but not DOPC TRAIL.[27] These results confirmed the mode of TRAIL-vesicle mediated cytotoxicity was through caspase-mediated apoptosis, and that concentrating TRAIL into vesicle membrane domains increased caspase activity.

Figure 12:
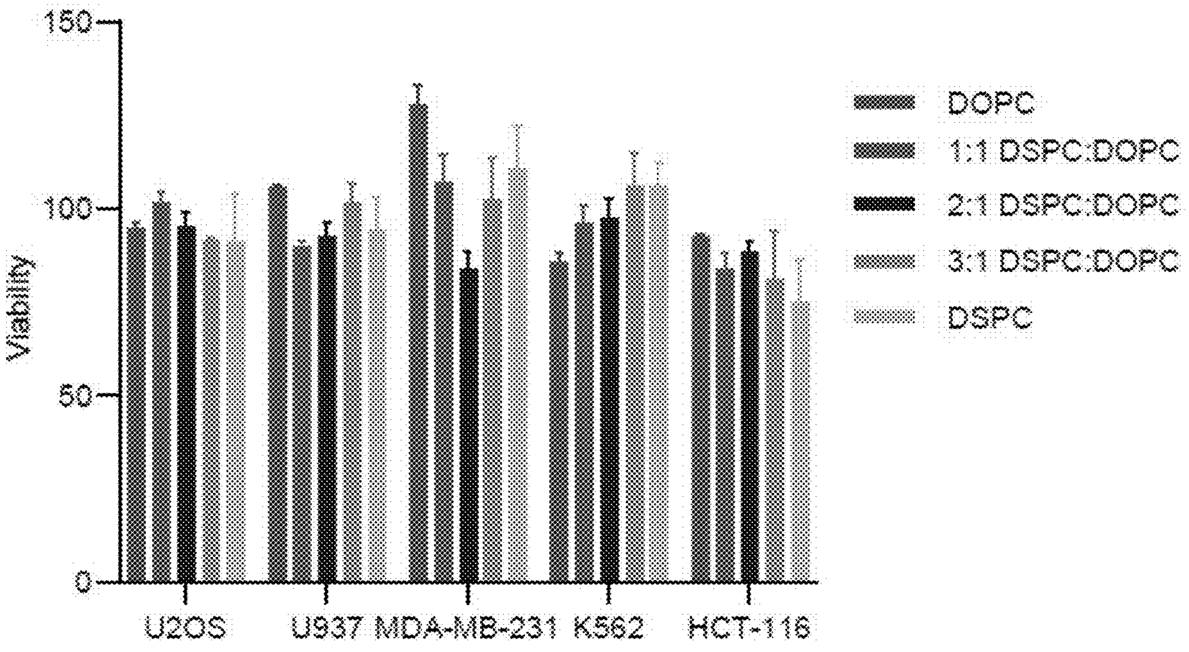
FIG. 12. Viability of different cell types incubated with unconjugated vesicles at 1 mM lipid concentration, which corresponds to the highest TRAIL concentration tested. Error bars represent SEM from n=3 different vesicle preparations.
Figure 13:
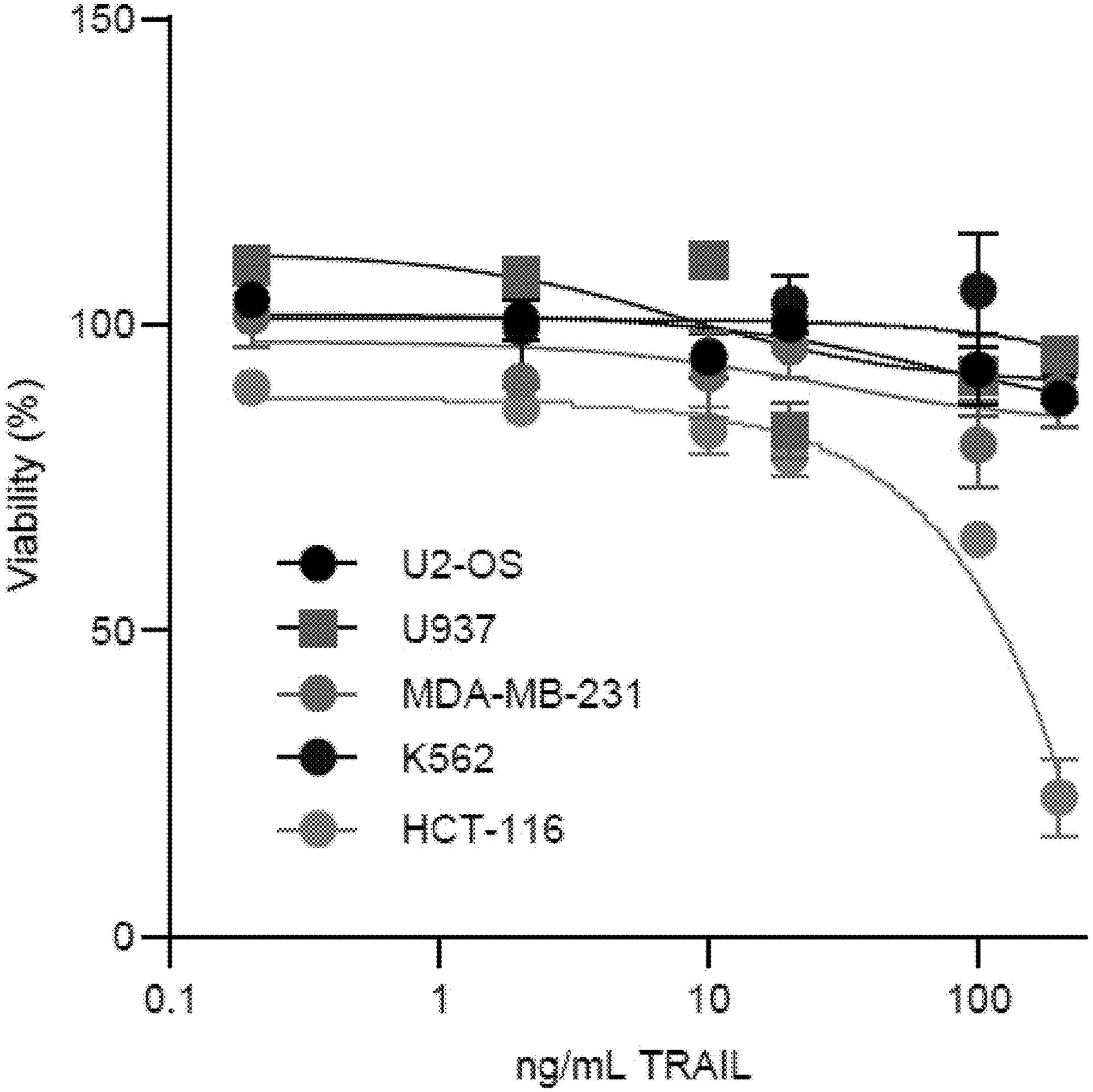
FIG. 13. Viability of different cell lines in the presence of DSPC TRAIL vesicles. HCT-116 is the only cell line that shows susceptibility to DSPC TRAIL vesicles, while other cell lines do not. Error bars represent SEM from n=3 different vesicle preparations. Concentration reported is the initial amount of TRAIL added to the vesicles during conjugation.
Figure 14:
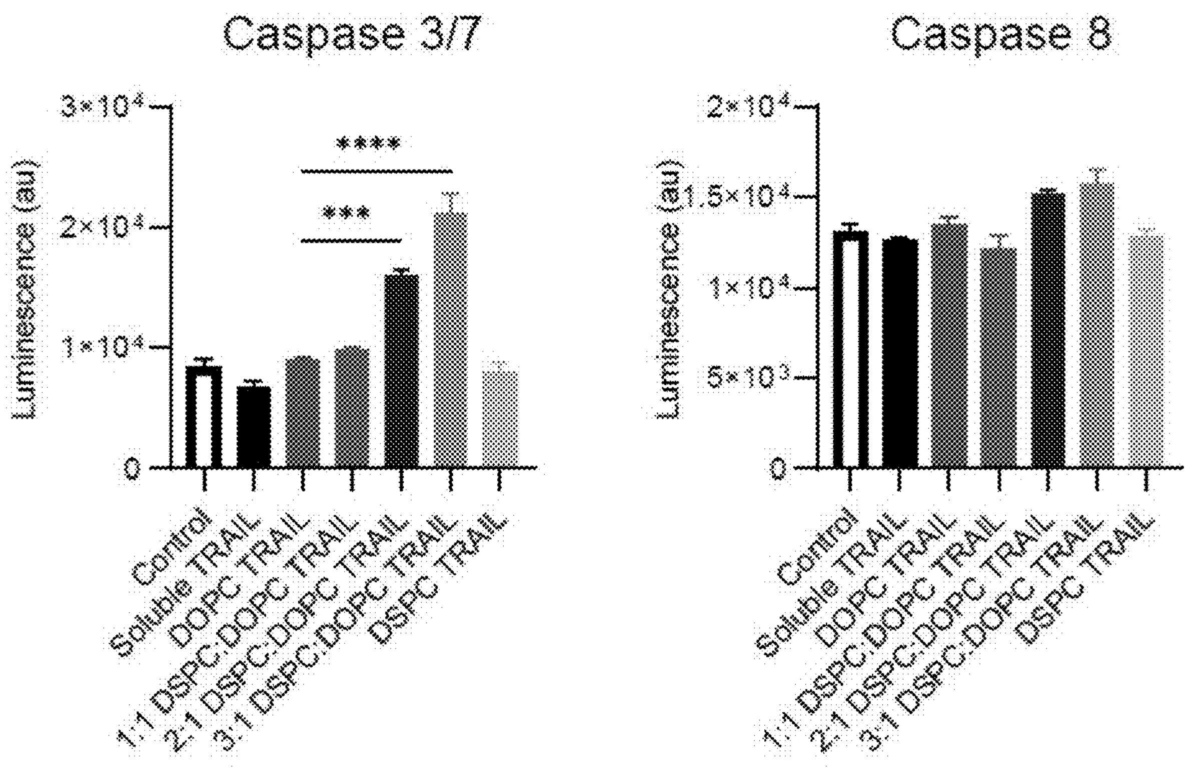
FIG. 14. Caspase 3/7 and Caspase 8 activity of U-937 cells incubated with 20 nM TRAIL vesicles and controls. Error bars represent SEM from n=3 different vesicle preparations. Significance test used was ANOVA. **$p<0.0001$, *$p<0.001$, **$p<0.01$, *$p<0.05$.

Finally, we wanted to assess the reproducibility of our system with other cell types. We assessed the cytotoxicity of phase-segregated TRAIL vesicles on 5 additional cancer cell lines: U2-OS, U937, MDA-MB-231, K562, and HCT-116 (FIG. 3A-E). Interestingly, we found that TRAIL segregation in membrane domains did not universally improve TRAIL cytotoxicity. Some cell types were sensitive to TRAIL segregation in domains similar to Jurkat cells (U2-OS, U937), while other cell types were showed no differences in viability between soluble TRAIL or domain-segregated TRAIL (K562, KDA-MB-231, and HCT-116). Again, treatment of cells with unconjugated vesicles at the highest lipid concentration showed no effects on viability, suggesting all observed cell death was dependent on TRAIL interactions with cells (FIG. 12). DSPC TRAIL vesicles again showed limited cytotoxicity (FIG. 13). We further tested caspase activity in U937 cells, one of the cells affected by TRAIL segregation in domains and saw similar trends to what was observed in Jurkat cells (FIG. 14). These results indicate that the capacity of spatial segregation to improve TRAIL mediated cell death is dependent on cell type.

Figure 4:
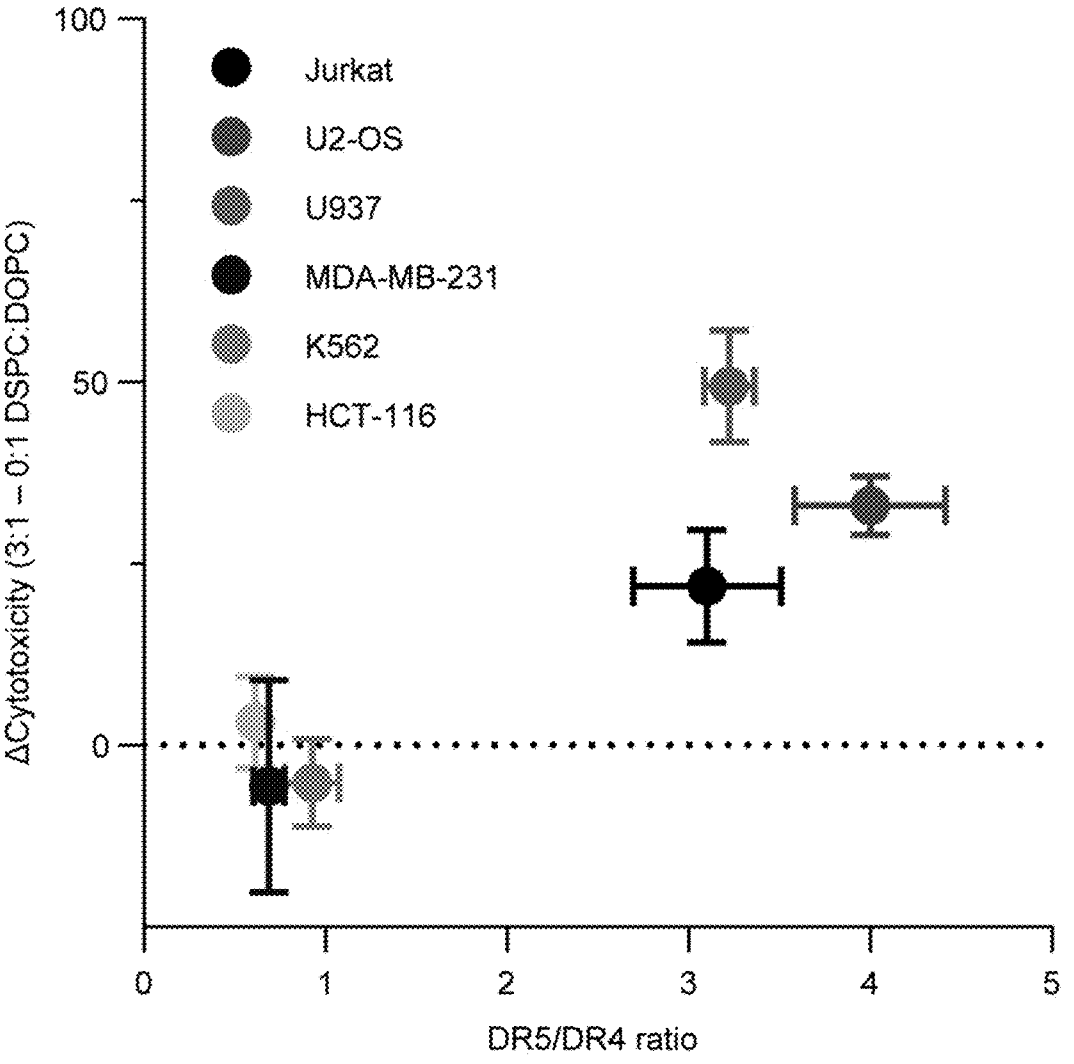
FIG. 4. Enhancement of TRAIL cytotoxicity with lipid domains is dependent on DR4 and DR5 expression levels in target cells. The DR5/DR4 ratio on target cells is shown relative to the resulting cytotoxicity difference between 3:1 DSPC:DOPC TRAIL vesicles to pure DOPC TRAIL vesicles. Cytotoxicity differences between vesicles containing domains and homogenous DOPC vesicles are only seen when DR5 is expressed higher than DR4. Error bar represents the SEM from n=6 (y-axis) and n=3 (x-axis).

We hypothesized that vesicle interactions with TRAIL receptors DR4 and DR5 may play a role in TRAIL sensitivity. Using flow cytometry, we measured the expression levels of DR4 and DR5 for each cell type (FIG. 3F-J). We compared the DR5/DR4 expression level to the difference in cell viability between cells incubated with 3:1 DSPC:DOPC (phase segregated) or DOPC (uniform) TRAIL vesicles and identified two distinct clusters (FIG. 4). Cells that predominantly expressed DR5 over DR4 were sensitive to TRAIL segregation in vesicle domains, while cells that expressed more or equivalent amounts of DR4 over DR5 showed no viability differences as a function of vesicle composition.

Discussion

Previous studies have shown that DR5 and DR4 can respond differentially to TRAIL. DR5 benefits from TRAIL oligomerization in order to activate apoptotic signaling.[28-30] In contrast, TRAIL oligomerization has less effect on DR4 activation.[28,31,32] DR4 resides in lipid rafts in certain cell types that are susceptible to TRAIL, rendering TRAIL oligomerization unnecessary because DR4 is likely already pre-organized[33]. Because DR4 can competitively bind TRAIL from DR5,[31,34,35] the relative differences in receptor expression should dictate the extent to which TRAIL density influences apoptotic signaling. We expect, therefore, that when DR5 is more prevalent on cell membranes than DR4, TRAIL density should become more important, and vesicles that localize TRAIL in phase segregated domains should affect the extent of apoptotic signaling. In contrast, when DR4 is more prevalent and TRAIL signaling occurs primarily through this receptor, the spatial density of TRAIL should be less important, which we observed in our studies. Besides competitive binding, DR4 and DR5 can also form heterocomplexes, which is not well understood but has been shown to predominantly signal through DR4 in pancreatic tumor cells.[36,37] Ultimately, the relative levels of DR4 and DR5 expression, and which receptor the cell predominately signals through, could affect the therapeutic strategy for TRAIL agonists.

Lipid domains provide a straightforward route to control the spatial density of a lipid-linked protein to signal cluster-dependent receptors like DR5. Our observations of TRAIL mediated cytotoxicity in cell types that express higher levels of DR5 relative to DR4 show that concentrating TRAIL in smaller lipid domains enhances cytotoxicity relative to vesicles with homogeneously distributed TRAIL. This observation is consistent with recent studies using DNA origami nanostructures: ligand spatial orientation improved apoptosis signaling in DR5 and Fas (CD95, a protein similar to DR5), with optimal inter-ligand distance at approximately 10 nm.[27,38] We do note that increasing vesicle binding to cells through TRAIL domains (FIG. 10) could have an effect on TRAIL cytotoxicity, but does not fully explain cytotoxicity differences because DSPC vesicles bind strongest without corresponding cytotoxicity. We therefore hypothesize that controlling TRAIL spatial orientation on lipid vesicles by using lipid domains most likely increases DR5-mediated apoptosis by approaching this critical inter-ligand distance. Further studies to characterize lipid domains in nanovesicles, however, will be required to more widely adopt this method. The domain size and number on lipid vesicles is dynamic and widely distributed similar to lipid rafts in cell membranes, and characterizing domains is extremely difficult.[39] Advances in cryo-EM have been developed to visualize lipid domains and protein localization in nanovesicles, which could allow us to better characterize how domain number and size could affect signaling.[40,41] Taken together, lipid phase separation is a facile method to control the spatial orientation of lipid linked proteins that can be readily incorporated into lipid vesicle design.

Vesicle phase separation is a useful technique to enhance protein-conjugated vesicles. Optimization of TRAIL density in other TRAIL nanoparticle approaches could enhance TRAIL therapeutics in vivo.[26,42-46] From a biomaterials perspective, controlled spatial conjugation of proteins can be applied to other types of vesicles with demonstrated phase separation, such as lipid-polymer hybrid vesicles[23,47] and polymersomes,[48,49] as well as in supported bilayer systems and nanoparticles for fundamental investigations into the effects of spatial arrangements on biological mechanisms.[50,51] Biological systems that are also known to be dependent on receptor clustering include immune signaling receptors[52,53] and receptor internalization.[54,55] Altogether, phase separated vesicles provide researchers a new tool to spatially control protein spacing for designing cell-mimetic systems and therapeutic nanoparticles.

Materials & Methods

Materials: 1,2-dioleoyl-sn-glycero-3-phosphocholine (DOPC), 1,2-distearoyl-sn-glycero-3-phosphocholine (DSPC), cholesterol (Chol), 1,2-dioleoyl-sn-glycero-3-[(N-(5-amino-1-carboxypentyl)iminodiacetic acid)succinyl] (nickel salt) (DGS-NTA-Ni), 1,2-distearoyl-sn-glycero-3-phosphoethanolamine-N-[methoxy(polyethylene glycol)-2000] (18:0 PEG2000-PE), 1,2-dioleoyl-sn-glycero-3-phosphoethanolamine-N-(lissamine rhodamine B sulfonyl) (18:1 Rho) were purchased from Avanti Polar Lipids. 1,2-dipalmitoyl-sn-glycero-3-phosphoethanolamine-N-(7-nitro-2-1,3-benzoxadiazol-4-yl) (16:0 NBD) was purchased from Invitrogen. Recombinant human TRAIL (His-tagged) was purchased from R&D Systems. CellTiter-Glo 2.0, Caspase-Glo 3/7, and Caspase-Glo 8 assay kits were purchased from Promega. Phosphate-buffered Saline (PBS) tablets were obtained from Sigma-Aldrich. Cell media components DMEM, RPMI, McCoy's 5A, fetal bovine serum (FBS) and penicillin streptomycin were purchased from Thermo Fisher (Gibco). Antibodies used for flow cytometry were anti-DR4 (clone HS101, Novus Biologicals), anti-DR5 (clone HS201, Novus Biologicals), isotype control (biotinylated clone MOPC-21, Biolegend), anti-mouse IgG (Cell Signaling Technology 7076) and APC-labeled anti-mouse IgG (Ab510115, Abcam).

Vesicle Formation: Small unilamellar vesicles (SUVs) were prepared using the thin film hydration method. Lipids dissolved in chloroform were dried down under a nitrogen stream to create lipid films and placed in a vacuum for 2 hours. Lipid films were rehydrated overnight with 1×PBS (290 mOsm, pH 7.3) at 60° C. Vesicles were briefly vortexed and extruded using an Avanti mini-extruder through a 100 nm polycarbonate filter placed on a hot plate at 70° C. for nine passes. Lipid compositions for each sample are provided in the supplement. Giant unilamellar vesicles (GUVs) were formed through electroformation using a Vesicle Prep Pro (Nanion). Vesicles were imaged usin FRET assays: Vesicles containing 0.5 mol % of 18:1 Rho (acceptor) and 0.5 mol % 16:0 NBD (donor) were added to a cuvette and the fluorescence was measured at 460 nm excitation and 535 nm $$\text{Normalized } FRET \text{ ratio} = \frac{F_{donor} / F_{acceptor}}{F_{donor,triton} / F_{acceptor,triton}} \quad (2)$$

and 583 nm emission using an Agilent Cary Eclipse Fluorimeter at 37° C. 0.1% Triton-X was added to each cuvette to lyse the vesicles to measure the unquenched fluorescence. For temperature ramp experiments, fluorescence was measured from 25° C. to 58° C. at 1° C. steps. FRET ratio and Normalized FRET ratio are defined as:

TRAIL conjugation to vesicles: To conjugate His-TRAIL onto vesicles, 1.0 mol % DGS-NTA lipid was incorporated into the vesicles to react with His-tag proteins, while 1.0 mol % 18:0 PEG2000-PE was added for vesicle stability. Vesicles were incubated with His-TRAIL (2 mM vesicles, 400 ng/mL TRAIL final concentration) for 1 hour at 37° C., then dialyzed overnight at 4° C. with a 100 kDa dialysis kit (Float-A-Lyzer G2, Repligen). Size, zeta potential, and number of vesicles after TRAIL conjugation were measured using a Malvern Zetasizer (for dynamic light scattering) and Nanosight (for nanoparticle tracking analysis). For FRET studies after TRAIL conjugation, 0.5 mol % of 18:1 Rho and 0.5 mol % 16:0 NBD were included in vesicle samples prior to TRAIL conjugation and FRET efficiency was measured as previously described.

Western blot analysis: Efficiency of TRAIL conjugation was assessed by western blot. Briefly, samples were mixed with Laemmli buffer (after purification to remove unconjugated TRAIL for vesicles) and boiled at 95° C. for 10 minutes (with and without SDS for reducing and non-reducing western blots, respectively). Samples were then loaded onto a 12% Mini-PROTEAN TGX Precast Protein Gel (Bio-Rad) and run at 100 V for at least 90 minutes. Wet transfer was performed onto an Immuno-Blot PVDF membrane (Bio-Rad) for 45 min at 100 V. Membranes were then blocked at room temperature for 1 hour in 5% milk in Tris-buffered saline with polysorbate 20 (TBST) pH 7.6 (20 mM Tris base, 150 mM NaCl, 0.1% polysorbate 20). Membranes were incubated in primary antibody solution (Mouse-anti-TRAIL (R&D Systems, MAB687), diluted 1:1000 in 5% milk in TBST) overnight at 4° C. Primary antibody was decanted and membrane was washed three times with TBST pH 7.6. Membranes were then incubated in secondary antibody solution (HRP-anti-Mouse (CST 7076), diluted 1:3000 in 5% milk in TBST pH 7.6) for 1 hour at room temperature. After incubation with secondary solution antibody, membranes were washed 3 times in TBST pH 7.6 and incubated with Clarity Western ECL Substrate (Bio-Rad) for 5 min and then imaged with an Azure C280. Images were then analyzed using the Fiji gel analysis tool.[56]

Cell culture: Jurkat, U937, HCT-116, and U2OS cells were obtained from ATCC without further authentication. MDA-MB-231 was obtained as a gift from the Mrksich lab from ATCC (Northwestern University) and K562 was obtained as a gift from the Leonard lab from ATCC (Northwestern University). Jurkat, U937, and K562 were cultured in RPMI 1640 supplemented with 10% FBS and 1% Pen/Strep. U205 and HCT-116 were cultured in McCoy's 5A supplemented with 10% FBS and 1% Pen/Strep. MDA-MB-231 were cultured in DMEM supplemented with 10% FBS and 1% Pen/Strep.

TRAIL cell viability assays: For adherent cells (MDA-MB-231, HCT-116, and U205), cells were detached from the plate using TrypLE Express and seeded in 96-black clear-bottom well plates at 5,000 cells/well the day before TRAIL addition to allow the cells to adhere. Suspension cells (Jurkat, U937, K562) were seeded at 25,000 cells/well the day of TRAIL addition. Vesicles in PBS and media (50% full media, 50% vesicles in PBS, 100 μL final volume) were incubated with cells at the indicated concentration (TRAIL is assumed to be 100% conjugated on vesicles when compared to soluble TRAIL) for 24 hours. After 24 hours, 100 μL of Celltiter Glo 2.0 solution was added to each well, allowed to mix for 5 minutes, then the luminescence was read with a plate reader (Molecular Devices). To analyze the percent cell viability, the luminescence of the treated well was divided by the luminescence of untreated cell wells and converted to a percentage using the following equation:

$$\text{Viability} = \frac{\text{Luminescence Treated Wells}}{\text{Average Luminescence of Untreated Wells}} * 100\%$$

Viability studies were performed with at least two different vesicle samples in triplicate. The correlation between given TRAIL concentration and lipid concentration is listed in Table 3, below.

TABLE 3

Correlation between given TRAIL concentration and lipid concentration

| TRAIL concentration (μg/mL) | Lipid concentration (nM) |
|---|---|
| 0.2 | 1 |
| 2 | 10 |
| 10 | 50 |
| 20 | 100 |
| 100 | 500 |
| 200 | 1000 |

Vesicle binding studies to Jurkat: Jurkat cells were seeded at 100,000 cells/well in a 96 U-bottom plate in flow buffer (1% FBS in PBS). Vesicles containing 0.5% 18:1 Rho at the indicated concentrations were incubated with Jurkat cells for one hour at room temperature (RT), washed two times, and resuspended in 200 μL of flow buffer. Cells were analyzed using a BD Fortessa LSRII using 550 nm excitation laser and 582/15 nm emission. Jurkat cells were gated based on forward versus side scatter (FSC-A vs. SSC-A) and single cells (FSC-A vs. FSC-H) and 10,000 single cell events were collected. Data was analyzed using FlowJo. Experiments were repeated in triplicate. For microscopy studies, TRAIL vesicles at 1 mM lipid concentration (corresponding to 200 ng/mL TRAIL) were incubated with Jurkat cells for 4 hours at 37° C., washed two times, then stained for nucleus (NucBlue Hoechst 33342, ThermoFisher) and viability (Sytox Green, ThermoFisher). Cells were imaged using a confocal microscope.

TRAIL caspase assays: Jurkat and U937 cells were seeded at 25,000 cells/well and 20 ng/mL soluble TRAIL or vesicle TRAIL was added to a 96-black clear-bottom well plate. Cells and TRAIL were incubated for 3 hours, then Caspase 3/7 and Caspase 8 detection kits (Promega) were added according to the manufacturer's protocols. Luminescence was read at every 5 minutes for 1 hour, and the max signal was used. Luminescence was normalized to the untreated cells.

DR4 and DR5 expression: DR4 and DR5 expression of cells was measured using flow cytometry. For Jurkat, MDA-MB-231, U2-OS, and HCT-116, cells were incubated with anti-DR4, anti-DR5, or isotype control at 1 μg/mL in flow buffer for 30 minutes at RT, washed, then 2 μg/mL of APC anti-mouse IgG was added for 30 minutes at RT. Cells were washed 2×, resuspended in flow buffer, then analyzed using BD Fortessa LSRII using 640 nm excitation and 670/14 nm emission. Cells were gated as previously described, and 10,000 single cell events were collected. Data was analyzed using FlowJo. For U937 and K562 cells, a modified protocol was used because of nonspecific binding of the isotype control. Cells were first incubated with isotype control in flow buffer for 30 minutes on ice, washed, then blocked with anti-mouse IgG in flow buffer for 30 minutes on ice. Blocked cells were untreated or incubated with anti-DR4 and anti-DR5 for 30 minutes at RT, washed, then incubated with 2 μg/mL of APC anti-mouse IgG for 30 minutes at RT. Cells were washed 2× and analyzed similarly to the other cells. Expression studies were done in triplicate, and the reported histogram expression data is a representation of the triplicate experiments.

Cryo-electron microscopy: 200-mesh lacey carbon grids were glow-discarged for 20 seconds in a Pelco easiGlow glow-discharger at 15 mA with a chamber pressure of 0.24 mBar. 4 uL of sample was then pipetted onto a grid and plunge-frozen into liquid ethane using an FEI Vitrobot Mark IV cryo plunge freezing robot for 5 seconds with a blotting pressure of 1. Grids were then loaded into a Gatan 626.5 cryo transfer holder, imaged at −180 C in a JEOL JEM1230 W emission TEM at 120 kV. Data was collected using Gatan Digital Micrograph software connected to a Gatan Orius SC1000 CCD Camera, Model 831.

Statistical Analysis: All nonlinear fits (three parameters), IC50 values, and significance tests were performed using Prism (Graphpad).

REFERENCES (1) Ye, K.; Wang, X.; Cao, L.; Li, S.; Li, Z.; Yu, L.; Ding, J. Matrix Stiffness and Nanoscale Spatial Organization of Cell-Adhesive Ligands Direct Stem Cell Fate. *Nano Lett.* 2015, 15, 4720-4729.

(2) Chen, Z.; Wholey, W.-Y.; Hassani Najafabadi, A.; Moon, J. J.; Grigorova, I.; Chackerian, B.; Cheng, W. Self-Antigens Displayed on Liposomal Nanoparticles above a Threshold of Epitope Density Elicit Class-Switched Autoreactive Antibodies Independent of T Cell Help. *J. Immunol.* 2020, 204, 335-347.

(3) Smith, M. R.; Tolbert, S. V.; Wen, F. Protein-Scaffold Directed Nanoscale Assembly of T Cell Ligands: Artificial Antigen Presentation with Defined Valency, Density, and Ratio. *ACS Synth. Biol.* 2018, 7, 1629-1639.

(4) Reuter, K. G.; Perry, J. L.; Kim, D.; Luft, J. C.; Liu, R.; DeSimone, J. M. Targeted PRINT Hydrogels: The Role of Nanoparticle Size and Ligand Density on Cell Association, Biodistribution, and Tumor Accumulation. *Nano Lett.* 2015, 15, 6371-6378.

(5) Zhang, Q.; Reinhard, B. M. Ligand Density and Nanoparticle Clustering Cooperate in the Multivalent Amplification of Epidermal Growth Factor Receptor Activation. *ACS Nano* 2018, 12, 10473-10485.

(6) Sanchez, L.; Yi, Y.; Yu, Y. Effect of Partial PEGylation on Particle Uptake by Macrophages. *Nanoscale* 2017, 9, 288-297.

(7) Lee, K.; Yu, Y. Janus Nanoparticles for T Cell Activation: Clustering Ligands to Enhance Stimulation. *J. Mater. Chem.* B 2017, 5, 4410-4415.

(8) Chen, B.; Jia, Y.; Gao, Y.; Sanchez, L.; Anthony, S. M.; Yu, Y. Janus Particles as Artificial Antigen-Presenting Cells for T Cell Activation. *ACS Appl. Mater. Interfaces* 2014, 6, 18435-18439.

(9) Liu, J.; Toy, R.; Vantucci, C.; Pradhan, P.; Zhang, Z.; Kuo, K. M.; Kubelick, K. P.; Huo, D.; Wen, J.; Kim, J.; Lyu, Z.; Dhal, S.; Atalis, A.; Ghosh-Choudhary, S. K.; Devereaux, E. J.; Gumbart, J. C.; Xia, Y.; Emelianov, S. Y.; Willett, N. J.; Roy, K. Bifunctional Janus Particles as Multivalent Synthetic Nanoparticle Antibodies (SNAbs) for Selective Depletion of Target Cells. *Nano Lett.* 2021, acs.nanolett.0c04833.

(10) Sezgin, E.; Levental, I.; Mayor, S.; Eggeling, C. The Mystery of Membrane Organization: Composition, Regulation and Roles of Lipid Rafts. *Nat. Rev. Mol. Cell Biol.* 2017, 18, 361-374.

(11) Veatch, S. L.; Keller, S. L. Separation of Liquid Phases in Giant Vesicles of Ternary Mixtures of Phospholipids and Cholesterol. *Biophys. J.* 2003, 85, 3074-3083.

(12) Rideau, E.; Dimova, R.; Schwille, P.; Wurm, F. R.; Landfester, K. Liposomes and Polymersomes: A Comparative Review towards Cell Mimicking. *Chem. Soc. Rev.* 2018, 47, 8572-8610.

(13) Elson, E. L.; Fried, E.; Dolbow, J. E.; Genin, G. M. Phase Separation in Biological Membranes: Integration of Theory and Experiment. dx.doi.org/10.1146/annurev.biophys.093008. 131238 2010, 39, 207-226.

(14) Imam, Z. I.; Kenyon, L. E.; Ashby, G.; Nagib, F.; Mendicino, M.; Zhao, C.; Gadok, A. K.; Stachowiak, J. C. Phase-Separated Liposomes Enhance the Efficiency of Macromolecular Delivery to the Cellular Cytoplasm. *Cell. Mol. Bioeng.* 2017, 10, 387-403.

(15) Trementozzi, A. N.; Imam, Z. I.; Mendicino, M.; Hayden, C. C.; Stachowiak, J. C. Liposome-Mediated Chemotherapeutic Delivery Is Synergistically Enhanced by Ternary Lipid Compositions and Cationic Lipids. *Langmuir* 2019, acs.langmuir.9b01965.

(16) von Karstedt, S.; Montinaro, A.; Walczak, H. Exploring the TRAILs Less Travelled: TRAIL in Cancer Biology and Therapy. *Nat. Rev. Cancer* 2017, 17, 352-366.

(17) Spitzer, D.; McDunn, J. E.; Plambeck-Suess, S.; Goedegebuure, P. S.; Hotchkiss, R. S.; Hawkins, W. G. A Genetically Encoded Multifunctional Trail Trimer Facilitates Cell-Specific Targeting and Tumor Cell Killing. *Mol. Cancer Ther.* 2010, 9, 2142-2151.

(18) De Miguel, D.; Gallego-Lleyda, A.; Ayuso, J. M.; Pejenaute-Ochoa, D.; Jarauta, V.; Marzo, I.; Fernández, L. J.; Ochoa, I.; Conde, B.; Anel, A.; Martinez-Lostao, L. High-Order TRAIL Oligomer Formation in TRAIL-Coated Lipid Nanoparticles Enhances DR5 Cross-Linking and Increases Antitumour Effect against Colon Cancer. *Cancer Lett.* 2016, 383, 250-260.

(19) Nair, P. M.; Flores, H.; Gogineni, A.; Marsters, S.; Lawrence, D. A.; Kelley, R. F.; Ngu, H.; Sagolla, M.; Komuves, L.; Bourgon, R.; Settleman, J.; Ashkenazi, A Enhancing the Antitumor Efficacy of a Cell-Surface Death Ligand by Covalent Membrane Display. *Proc. Natl. Acad. Sci.* 2015, 112, 5679-5684.

(20) De Miguel, D.; Gallego-Lleyda, A.; Anel, A.; Martinez-Lostao, L. Liposome-Bound TRAIL Induces Superior DR5 Clustering and Enhanced DISC Recruitment in Histiocytic Lymphoma U937 Cells. *Leuk. Res.* 2015, 39, 657-666.

(21) Zhao, J.; Wu, J.; Heberle, F. A.; Mills, T. T.; Klawitter, P.; Huang, G.; Costanza, G.; Feigenson, G. W. Phase Studies of Model Biomembranes: Complex Behavior of DSPC/DOPC/Cholesterol. *Biochim. Biophys. Acta—Biomembr.* 2007, 1768, 2764-2776.

(22) Shishina, A. K.; Kovrigina, E. A.; Galiakhmetov, A. R.; Rathore, R.; Kovrigin, E. L. Study of Förster Resonance Energy Transfer to Lipid Domain Markers Ascertains Partitioning of Semisynthetic Lipidated N-Ras in Lipid Raft Nanodomains. *Biochemistry* 2018, 57, 872-881.

(23) Dao, T. P. T.; Fernandes, F.; Er-Rafik, M.; Salva, R.; Schmutz, M.; Brûlet, A.; Prieto, M.; Sandre, O.; Le Meins, J. F. Phase Separation and Nanodomain Formation in Hybrid Polymer/Lipid Vesicles. *ACS Macro Lett.* 2015, 4, 182-186.

(24) Almeda, D.; Wang, B.; Auguste, D. T. Minimizing Antibody Surface Density on Liposomes While Sustaining Cytokine-Activated EC Targeting. *Biomaterials* 2015, 41, 37-44.

(25) Gunawan, R. C.; Auguste, D. T. The Role of Antibody Synergy and Membrane Fluidity in the Vascular Targeting of Immunoliposomes. *Biomaterials* 2010, 31, 900-907.

(26) Le, D. H. T.; Commandeur, U.; Steinmetz, N. F. Presentation and Delivery of Tumor Necrosis Factor-Related Apoptosis-Inducing Ligand via Elongated Plant Viral Nanoparticle Enhances Antitumor Efficacy. *ACS Nano* 2019, 13, acsnano.8b09462.

(27) Berger, R. M. L.; Weck, J. M.; Kempe, S. M.; Hill, O.; Liedl, T.; Radler, J. O.; Monzel, C.; Heuer-Jungemann, A. Nanoscale FasL Organization on DNA Origami to Decipher Apoptosis Signal Activation in Cells. *Small* 2021, 17, 2101678.

(28) Natoni, A.; MacFarlane, M.; Inoue, S.; Walewska, R.; Majid, A.; Knee, D.; Stover, D. R.; Dyer, M. J. S.; Cohen, G. M. TRAIL Signals to Apoptosis in Chronic Lymphocytic Leukaemia Cells Primarily through TRAIL-R1 Whereas Cross-Linked Agonistic TRAIL-R2 Antibodies Facilitate Signalling via TRAIL-R2. *Br. J. Haematol.* 2007, 139, 568-577.

(29) Berg, D.; Stühmer, T.; Siegmund, D.; Müller, N.; Giner, T.; Dittrich-Breiholz, 0.; Kracht, M.; Bargou, R.; Wajant, H. Oligomerized Tumor Necrosis Factor-Related Apoptosis Inducing Ligand Strongly Induces Cell Death in Myeloma Cells, but Also Activates Proinflammatory Signaling Pathways. *FEBS J.* 2009, 276, 6912-6927.

(30) Beyrath, J.; Chekkat, N.; Smulski, C. R.; Lombardo, C. M.; Lechner, M.-C.; Seguin, C.; Decossas, M.; Spanedda, M. V.; Frisch, B.; Guichard, G.; Fournel, S.; Beyrath, J.; Chekkat, N.; Smulski, C. R.; Lombardo, C. M.; Lechner, M.-C.; Seguin, C.; Decossas, M.; Spanedda, M. V.; Frisch, B.; Guichard, G.; Fournel, S. Synthetic Ligands of Death Receptor 5 Display a Cell-Selective Agonistic Effect at Different Oligomerization Levels. *Oncotarget* 2016, 7, 64942-64956.

(31) Kelley, R. F.; Totpal, K.; Lindstrom, S. H.; Mathieu, M.; Billeci, K.; DeForge, L.; Pai, R.; Hymowitz, S. G.; Ashkenazi, A. Receptor-Selective Mutants of Apoptosis-Inducing Ligand 2/Tumor Necrosis Factor-Related Apoptosis-Inducing Ligand Reveal a Greater Contribution of Death Receptor (DR) 5 than DR4 to Apoptosis Signaling. *J. Biol. Chem.* 2005, 280, 2205-2212.

(32) Wajant, H.; Moosmayer, D.; Wüest, T.; Bartke, T.; Gerlach, E.; Schönherr, U.; Peters, N.; Scheurich, P.; Pfizenmaier, K. Differential Activation of TRAIL-R1 and -2 by Soluble and Membrane TRAIL Allows Selective Surface Antigen-Directed Activation of TRAIL-R2 by a Soluble TRAIL Derivative. *Oncogene* 2001, 20, 4101-4106.

(33) Marconi, M.; Ascione, B.; Ciarlo, L.; Vona, R.; Garofalo, T.; Sorice, M.; Gianni, A. M.; Locatelli, S. L.; Carlo-Stella, C.; Malorni, W.; Matarrese, P. Constitutive Localization of DR4 in Lipid Rafts Is Mandatory for TRAIL-Induced Apoptosis in B-Cell Hematologic Malignancies. *Cell Death Dis.* 2013, 4, e863-e863.

(34) Reis, C. R.; van der Sloot, A. M.; Natoni, A.; Szegezdi, E.; Setroikromo, R.; Meijer, M.; Sjollema, K.; Stricher, F.; Cool, R. H.; Samali, A.; Serrano, L.; Quax, W. J. Rapid and Efficient Cancer Cell Killing Mediated by High- Affinity Death Receptor Homotrimerizing TRAIL Variants. *Cell Death Dis.* 2010, 1, e83-e83.
(35) Bin, L.; Thorburn, J.; Thomas, L. R.; Clark, P. E.; Humphreys, R.; Thorburn, A. Tumor-Derived Mutations in the TRAIL Receptor DR5 Inhibit TRAIL Signaling through the DR4 Receptor by Competing for Ligand Binding. *J. Biol. Chem.* 2007, 282, 28189-28194.
(36) Lemke, J.; Noack, A.; Adam, D.; Tchikov, V.; Bertsch, U.; Wider, C.; Schütze, S.; Wajant, H.; Kalthoff, H.; Trauzold, A. TRAIL Signaling Is Mediated by DR4 in Pancreatic Tumor Cells despite the Expression of Functional DR5. *J. Mol. Med.* 2010, 88, 729-740.
(37) Kischkel, F. C.; Lawrence, D. A.; Chuntharapai, A.; Schow, P.; Kim, K. J.; Ashkenazi, A. Apo2L/TRAIL-Dependent Recruitment of Endogenous FADD and Caspase-8 to Death Receptors 4 and 5. *Immunity* 2000, 12, 611-620.
(38) Wang, Y.; Baars, I.; Fördös, F.; Högberg, B. Clustering of Death Receptor for Apoptosis Using Nanoscale Patterns of Peptides. *ACS Nano* 2021, 15, 9614-9626.
(39) Rosetti, C. M.; Mangiarotti, A.; Wilke, N. Sizes of Lipid Domains: What Do We Know from Artificial Lipid Membranes? What Are the Possible Shared Features with Membrane Rafts in Cells? *Biochim. Biophys. Acta—Biomembr.* 2017, 1859, 789-802.
(40) Cornell, C. E.; Mileant, A.; Thakkar, N.; Lee, K. K.; Keller, S. L. Direct Imaging of Liquid Domains in Membranes by Cryo-Electron Tomography. *Proc. Natl. Acad. Sci. U.S.A.* 2020, 117, 19713-19719.
(41) Heberle, F. A.; Doktorova, M.; Scott, H. L.; Skinkle, A. D.; Waxham, M. N.; Levental, I. Direct Label-Free Imaging of Nanodomains in Biomimetic and Biological Membranes by Cryogenic Electron Microscopy. *Proc. Natl. Acad. Sci. U.S.A.* 2020, 117, 19943-19952.
(42) Zakaria, A. B.; Picaud, F.; Rattier, T.; Pudlo, M.; Saviot, L.; Chassagnon, R.; Lherminier, J.; Gharbi, T.; Micheau, O.; Herlem, G. Nanovectorization of TRAIL with Single Wall Carbon Nanotubes Enhances Tumor Cell Killing. *Nano Lett.* 2015, 15, 891-895.
(43) Mitchell, M. J.; Webster, J.; Chung, A.; Guimarães, P. P. G.; Khan, O. F.; Langer, R. Polymeric Mechanical Amplifiers of Immune Cytokine-Mediated Apoptosis. *Nat. Commun.* 2017, 8, 14179.
(44) Mitchell, M. J.; Wayne, E.; Rana, K.; Schaffer, C. B.; King, M. R. TRAIL-Coated Leukocytes That Kill Cancer Cells in the Circulation. *Proc. Natl. Acad. Sci.* 2014, 111, 930-935.
(45) Jyotsana, N.; Zhang, Z.; Himmel, L. E.; Yu, F.; King, M. R. Minimal Dosing of Leukocyte Targeting TRAIL Decreases Triple-Negative Breast Cancer Metastasis Following Tumor Resection. *Sci. Adv.* 2019, 5, eaaw4197.
(46) Ortiz-Otero, N.; Marshall, J. R.; Lash, B. W.; King, M. R. Platelet Mediated TRAIL Delivery for Efficiently Targeting Circulating Tumor Cells. *Nanoscale Adv.* 2020, 2, 3942-3953.
(47) Brodszkij, E.; Westensee, I. N.; Bertelsen, M.; Gal, N.; Boesen, T.; Städler, B. Polymer-Lipid Hybrid Vesicles and Their Interaction with HepG2 Cells. *Small* 2020, 16, 1906493.
(48) Rideau, E.; Wurm, F. R.; Landfester, K. Membrane Engineering: Phase Separation in Polymeric Giant Vesicles. *Small* 2020, 16, 1905230.
(49) Christian, D. A.; Tian, A.; Ellenbroek, W. G.; Levental, I.; Rajagopal, K.; Janmey, P. A.; Liu, A. J.; Baumgart, T.; Discher, D. E. Spotted Vesicles, Striped Micelles and Janus Assemblies Induced by Ligand Binding. *Nat. Mater.* 2009 810 2009, 8, 843-849.
(50) Rinaldin, M.; Fonda, P.; Giomi, L.; Kraft, D. J. Geometric Pinning and Antimixing in Scaffolded Lipid Vesicles. *Nat. Commun.* 2020, 11, 4314.
(51) Rabanel, J.-M.; Adibnia, V.; Tehrani, S. F.; Sanche, S.; Hildgen, P.; Banquy, X.; Ramassamy, C. Nanoparticle Heterogeneity: An Emerging Structural Parameter Influencing Particle Fate in Biological Media? *Nanoscale* 2019, 11, 383-406.
(52) Kern, N.; Dong, R.; Douglas, S. M.; Vale, R. D.; Morrissey, M. A. Tight Nanoscale Clustering of Fcγ Receptors Using DNA Origami Promotes Phagocytosis. *Elife* 2021, 10, 1-29.
(53) Perica, K.; Tu, A.; Richter, A.; Bieler, J. G.; Edidin, M.; Schneck, J. P. Magnetic Field-Induced T Cell Receptor Clustering by Nanoparticles Enhances T Cell Activation and Stimulates Antitumor Activity. *ACS Nano* 2014, 8, 2252-2260.
(54) Gonda, A.; Kabagwira, J.; Senthil, G. N.; Wall, N. R. Internalization of Exosomes through Receptor-Mediated Endocytosis. *Mol. Cancer Res.* 2019, 17, 337-347.
(55) Moody, P. R.; Sayers, E. J.; Magnusson, J. P.; Alexander, C.; Boni, P.; Watson, P.; Jones, A. T. Receptor Crosslinking: A General Method to Trigger Internalization and Lysosomal Targeting of Therapeutic Receptor: Ligand Complexes. *Mol. Ther.* 2015, 23, 1888-1898.
(56) Schindelin, J.; Arganda-Carreras, I.; Frise, E.; Kaynig, V.; Longair, M.; Pietzsch, T.; Preibisch, S.; Rueden, C.; Saalfeld, S.; Schmid, B.; Tinevez, J.-Y.; White, D. J.; Hartenstein, V.; Eliceiri, K.; Tomancak, P.; Cardona, A. Fiji: An Open-Source Platform for Biological-Image Analysis. *Nat. Methods* 2012, 9, 676-682.

What is claimed:

1. A composition comprising phase separated nanoparticles comprising:

liquid-ordered ($L_o$) domains comprising 1,2-distearoyl-sn-glycero-3-phosphocholine (DSPC);

liquid-disordered ($L_d$) domains comprising 1,2-dioleoyl-sn-glycero-3-phosphocholine (DOPC);

a saturated PEG-modified lipid selected from 1.2-distearoyl-sn-glycero-3-phosphoethanolamine-N-[methoxy (polyethylene glycol)-2000] (18:0 PEG2000-PE), 1,2-distearoyl-sn-glycero-3-phosphoethanolamine-N-[methoxy (polyethylene glycol)-1000] (18:0 PEG1000 PE), 1,2-distearoyl-sn-glycero-3-phosphoethanolamine-N-[methoxy (polyethylene glycol)-500] (18:0 PEG500 PE), and 1,2-distearoyl-sn-glycero-3-phosphoethanolamine-N-[methoxy (polyethylene glycol)-5000] (18:0 PEG5000 PE);

cholesterol;

and an unsaturated lipid conjugated to TNF-related apoptosis inducing ligand (TRAIL) at 1 mol %;

wherein a ratio of the DSPC to the DOPC is 2:1 or 3:1.

2. The composition of claim 1, further comprising a saturated lipid selected from dipalmitoylphosphatidylcholine (DPPC), 1,2-distearoyl-sn-glycero-3-phospho-L-serine (DSPS), 1,2-dipalmitoyl-sn-glycero-3-phosphoserine (DPPS), 1,2-stearoyl-3-trimethylammonium-propane (DSTAP), 1,2-dipalmitoyl-sn-glycero-3-phosphoglycerol (DPPG), 1,2-distearoyl-sn-glycero-3-phosphoglycerol (DSPG), dipalmitoylphosphatidic acid (DPPA), and 1,2-distearoyl-sn-glycero-3-phosphate (DSPA).

3. The composition of claim 1, further comprising an unsaturated lipid selected from L-α-dioleoylphosphatidyl ethanolamine (DOPE), 1,2-dioleoyl-sn-glycero-3-phospho-L-serine (DOPS), 1,2-dioleoyl-3-trimethylammonium-propane (DOTAP), 1,2-Dioleoyl-sn-glycero-3-phosphoglycerol (DOPG), and dioleoylphosphatidic acid (DOPA).

4. The composition of claim 1, wherein the unsaturated lipid conjugated to TRAIL is labeled; and wherein TRAIL comprises a tag that binds to the label.

5. The composition of claim 4, wherein the unsaturated lipid is DGS-NTA-Ni.

6. The composition of claim 1, wherein the cholesterol is at 30 mol %.

7. The composition of claim 1, wherein the phase separated nanoparticles further comprise a fluorophore-modified lipid selected from 1,2-dioleoyl-sn-glycero-3-phosphoethanolamine-N-(lissamine rhodamine B sulfonyl) (18:1 Rho), 1,2-dipalmitoyl-sn-glycero-3-phosphoethanolamine-N-(7-nitro-2-1,3-benzoxadiazol-4-yl) (16:0 NBD), 1,2-dioleoyl-sn-glycero-3-phosphoethanolamine-N-(Cyanine 5.5) (18:1 Cy5.5 PE), 1,2-distearoyl-sn-glycero-3-phosphoethanolamine-N-(Cyanine 5.5) (18:0 Cy5.5 PE), 1,2-dioleoyl-sn-glycero-3-phosphoethanolamine-N-(Cyanine 7) (18:1 Cy7 PE), and 1,2-distearoyl-sn-glycero-3-phosphoethanolamine-N-(Cyanine 7) (18:0 Cy7 PE).

8. The composition of claim 1, wherein the saturated PEG-modified lipid is 18:0 PEG2000-PE.

9. The composition of claim 4, wherein the tag is a His tag.

10. The composition of claim 1, wherein the saturated PEG-modified lipid is at 1 mol %.

* * * * *